(12) United States Patent
Sharma et al.

(10) Patent No.: US 8,747,811 B2
(45) Date of Patent: Jun. 10, 2014

(54) PERYLENEQUINONE DERIVATIVES AND USES THEREOF

(71) Applicant: Quest Pharmatech, Inc., Edmonton (CA)

(72) Inventors: Sanjay K. Sharma, Edmonton (CA); Thomas Woo, Edmonton (CA); Selvaraj Naicker, Edmonton (CA)

(73) Assignee: Quest Pharmatech Inc., Edmonton (CA)

( * ) Notice: Subject to any disclaimer, the term of this patent is extended or adjusted under 35 U.S.C. 154(b) by 0 days.

(21) Appl. No.: 14/012,865

(22) Filed: Aug. 28, 2013

(65) Prior Publication Data

US 2014/0072512 A1    Mar. 13, 2014

Related U.S. Application Data

(60) Continuation of application No. 13/792,456, filed on Mar. 11, 2013, which is a division of application No. 11/722,423, filed as application No. PCT/CA2006/001234 on Jul. 28, 2006, now Pat. No. 8,506,931.

(60) Provisional application No. 60/706,755, filed on Aug. 10, 2005.

(51) Int. Cl.
*A61K 49/00* (2006.01)
*A61B 5/055* (2006.01)

(52) U.S. Cl.
USPC .......................................... 424/9.1; 424/9.3

(58) Field of Classification Search
USPC ........................................................ 424/9.1
See application file for complete search history.

*Primary Examiner* — Michael G Hartley
*Assistant Examiner* — Melissa Perreira
(74) *Attorney, Agent, or Firm* — Benoît & Côté Inc.

(57) ABSTRACT

The present invention relates to compounds which are perylenequinone derivatives, their stereoisomers and atropisomers. These compounds can be particularly useful as photosensitizers or sononsensitizers in photodynamic or sonodynamic therapy. The invention also relates to various methods for using these compounds in photodynamic and/or sonodynamic therapy. The compounds also are useful as therapeutic agents for treating various hyperproliferative disorders.

30 Claims, 25 Drawing Sheets

Control 5 hours

Control (day 1)

Control Drug Only, No Light Day 7

SL052 with Light treatment Day 35

PERYLENEQUINONE DERIVATIVES AND USES THEREOF

CROSS REFERENCE TO RELATED APPLICATION

This application is a continuation of U.S. patent application Ser. No. 13/792,456, filed Mar. 11, 2013, which is a divisional application of U.S. patent application Ser. No. 11/722,423, filed Jun. 21, 2007, now U.S. Pat. No. 8,506,931, issued Aug. 13, 2013, which is a national stage application under 35 U.S.C. 371 of PCT Application No. PCT/CA2006/001234, having an international filing date of Jul. 28, 2006 which designated the United States, which PCT application claimed the benefit of U.S. Provisional Application Ser. No. 60/706,755, filed Aug. 10, 2005, each of which is incorporated herein by reference.

FIELD OF THE INVENTION

The present invention relates to the field of medicinal chemistry. In particular, it relates to perylenequinone derivatives. Such compounds can be used in photodynamic therapy or as photosensitizers. These compounds, which are useful as therapeutic agents, can also be used for treating various hyperproliferative disorders.

BACKGROUND OF THE INVENTION

Photodynamic therapy (PDT) is a treatment modality using light of an appropriate wavelength to activate a photosensitizer in the presence of oxygen, which generates active oxygen species of high reactivity then the target molecule thereby leading to the tissue damage. Owing to its advantages such as relative selectivity in most sites, its compatibility with other treatment, its repeatability, its ease of delivery etc., PDT is slowly finding its place as a useful method for the treatment of certain cancers or clinical situation, such as early stage cancer of the lungs, esophagus, stomach, cervix, cervical dysplasia etc. Prime features of the ideal photosensitizer are low dark toxicity, selective accumulation in malignant cells, appropriate retention time, absorption in the phototherapeutic window (600-900 nm) and high triplet yield with long time to decay. Various photosensitizers have been used for PDT, the first generation of the photosensitizers is based on porphyrin structure, Photofrin II®, for disseminated i.p. malignancies have received most of the attention. Limitation of a currently used photosensitizer, Photofrin-II®, which include prolonged cutaneous photosensitivity, batch variability, difficulty with purification, monomeric form as complicated serum, normal tissue and the tumor pharmacokinetics. The poor light absorption in the therapeutic window is suboptimal in terms of light penetration in tissues. These undesired features have prompted the development of second generation of photosensitizers more amenable to site directed chemical modification to improve physicochemical, pharmacological and clinical properties (Miller et al. *Drug Devel. Res.*, 42, 1997, 182).

Lown and co-workers (Lown J. W. et al. *Tetrahedron*, 48, 1992, 45), (Lown J. W. et al. *Photochem. Photobiol.*, 52, 1990, 609) have addressed this problem associated with Photofrin-II® by modifying perylenequinonoid pigments (PQP), which are derived from the natural sources (especially from fungus) exhibits intriguing stereo chemical features and possess interesting biological activities. Of these, hypocrellin A (compound (1)) and hypocrellin B (compound 2)), which are lipid-soluble perylenequinone derivatives (Chen et al. *Liebigs Ann. Chem.*, 1981, 1880) (Kishi et al. *Planta Med.*, 57, 1991, 376) isolated from the fungus *Hypocrella bambuase* sacc a parasitic fungus of the *Sinarundinaria* species growing abundantly in the southern China in the region of Yunnan Provience, southeastern region of Tibet and certain parts of Sri Lanka, have served as the starting point for the development of new improved photosensitizers.

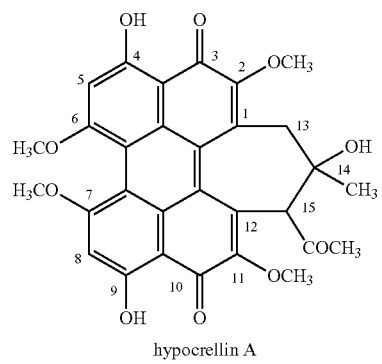

hypocrellin A

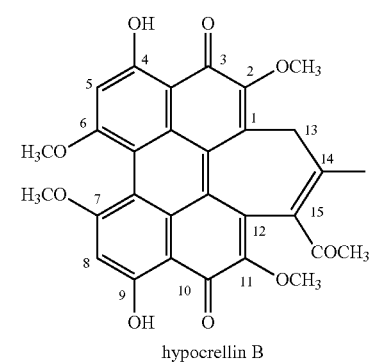

hypocrellin B

Hypocrellin A and B have been intensively investigated because of their light induced anti tumor (Zhang et al. *Photochem Photobiol*, 69(5), 1999, 582), (Zhang et al. *J. Photochem Photobiol.* 44, 1998, 21) and antiviral activity (Hirayama et al. *Photochem. Photobiol.* 66(5), 1997, 697) termed, technically known as Photodynamic therapy (PDT). Hypocrellins were first recognized as potential photosensitizers for PDT (Wan et al. *Kexue Tongbao* (English Edition), 26, 1981, 1040-1042) in the early 1980s. Hypocrellins are efficient singlet oxygen generators during photochemical reactions and may also exert photosensitization via radical mechanisms, which may confer a degree of independence from classical type II oxygen dependent photochemical mechanism. Preliminary acute and chronic dose escalation studies of hypocrellins and their derivatives have failed to demonstrate any toxic properties in rodents to "total-body" levels of 50 m mol/Kg or approximately two logs higher than typical in vitro photosensitizing dose. Hypocrellins have several advantages over the other photosensitizers like easy preparation and purification, low toxicity, high stability, no aggregation, rapid metabolism, low side effects and selective localization in cancer tissues. However the natural occurring compounds are only lipid soluble and exhibit little absorption in the photodynamic window which limits their application in PDT. In order to overcome these issues, i.e. lack of photodynamic activity and water solubility, a large number of hypocrellin-based compounds have been synthesized and biologically evaluated in the last twenty years.

Therefore, various approaches have been adopted to increase the red absorption of the hypocrellin B (Shangjie et al. *Photochem. and Photobiol.*, 78(4), 2003, 411), (US Patent application published under No. US2004/0092557 A1).

However, there is still a clear need for improvement. It would thus be highly desirable to be provided with a compound having an enhanced photodynamic activity as compared to hypocrellin A and hypocrellin B.

SUMMARY OF THE INVENTION

In accordance with one aspect of the present invention there is provided compounds of formula (Ia) or (Ib) or stereoisomer or atropisomers thereof:

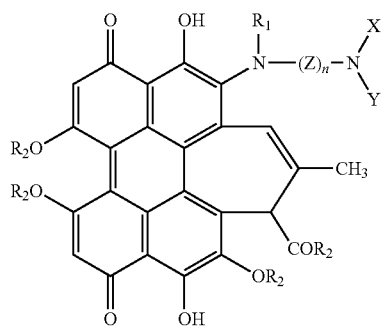

(Ia)

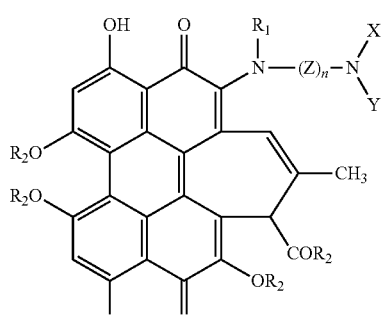

(Ib)

wherein

X and Y are independently hydrogen, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_8$-$C_{12}$ aryl, $C_8$-$C_{12}$ aralkyl, $C_1$-$C_{12}$ heterocyclyl, $C_1$-$C_{12}$ heteroaryl, —$COR_1$, —$(CH_2)_mOR_1$, —$CO_2H$, —$CO_2R_1$, —$C(O)N(R_1)_2$, —$C(O)NH(R_1)$, or —$C(O)NH_2$, said $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl being unsubstituted or substituted with at least one substituent selected from the group consisting of a halogen atom, hydroxy, carboxy, thiol, azide, nitro, $C_1$-$C_8$ deuterated alkyl group comprising at least one deuterated atom, —COH, —$COR_1$, —$(CH_2)_mOR_1$, —$CO_2H$, —$CO_2R_1$, —$C(O)N(R_1)_2$—$C(O)NH(R_1)$, —$C(O)NH_2$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl;

Z is —$CH_2$—, —$CHR_3$—, —$CH_2$—CH=CH—, —$CHR_3$—CH=CH—, or —$CH_2$—CH=$CR_3$—;

$R_1$ is a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

each $R_2$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

$R_3$ is halogen atom, hydroxy, sulphydral(-SH), an amino acid residue, carboxy, thiol, azide, nitro, $SO_3H$, —COH, —$COR_1$, —$(CH_2)_mOR_1$, —$CO_2H$, —$CO_2R_1$, —$C(O)N(R_1)_2$—$C(O)NH(R_1)$, —$C(O)NH_2$, —$HNC(O)R_1$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, or $C_1$-$C_{12}$ heteroaryl;

n is an integer having a value of 1 to 13; and m is an integer having a value of 1 to 13, or a pharmaceutically acceptable salt thereof.

The person skilled in the art would clearly recognize that compounds of formulas (Ia) and (Ib) are tautomers and that they may coexist at equilibrium. Under certain circumstances one of them may be more stable and therefore the equilibrium may be accordingly shifted towards this tautomer. Under other particular circumstances it may be possible that only one of the tautomers is substantially present. It will also be understood that the present invention also covers any other tautomers or isomers of the compounds of formulas (Ia) and (Ib).

In accordance with another aspect of the present invention there is provided compounds of formula (IIa) or (IIb) or stereoisomer or atropisomer thereof:

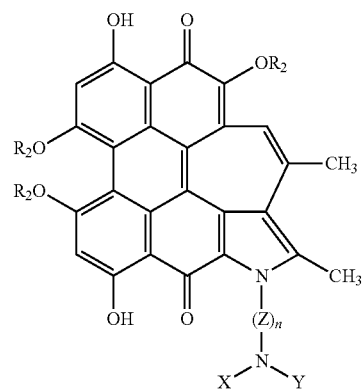

(IIa)

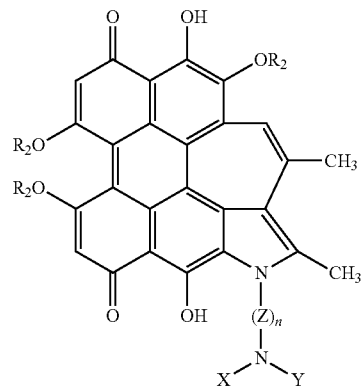

(IIb)

wherein

X and Y are independently hydrogen, $C_1$-$C_8$, alkyl, $C_2$-$C_8$ alkenyl, $C_2$-$C_8$ alkynyl, $C_3$-$C_8$ cycloalkyl, $C_4$-$C_{10}$ cycloalkenyl, $C_8$-$C_{12}$ aryl, $C_6$-$C_{12}$ aralkyl, $C_1$-$C_{12}$ heterocyclyl, $C_1$-$C_{12}$ heteroaryl, —$COR_1$, —$(CH_2)_mOR_1$, —$CO_2H$, —$CO_2R_1$, —$C(O)N(R_1)_2$, —$C(O)NH(R_1)$, or —$C(O)NH_2$, said $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl being unsubstituted or substituted with at least one substituent selected from the group consisting of a halogen atom, hydroxy, carboxy, thiol, azide, nitro, $C_1$-$C_8$ deuterated alkyl group comprising at least one deuterated atom, —COH, —COR$_1$, —(CH$_2$)$_m$OR$_1$, —CO$_2$H, —CO$_2$R$_1$, —C(O)N(R$_1$)$_2$—C(O)NH(R$_1$), —C(O)NH$_2$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl;

Z is —CH$_2$—, —CHR$_3$—, —CH$_2$—CH=CH—, —CHR$_3$—CH=CH—, or —CH$_2$—CH=CR$_3$—;

$R_1$ is a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

each $R_2$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

$R_3$ is halogen atom, hydroxy, sulphydral(-SH), an amino acid residue, carboxy, thiol, azide, nitro, SO$_3$H, —COH, —COR$_1$, —(CH$_2$)$_m$OR$_1$, —CO$_2$H, —CO$_2$R$_1$, —C(O)N(R$_1$)$_2$—C(O)NH(R$_1$), —C(O)NH$_2$, —HNC(O)R$_1$, $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, or $C_1$-$C_{12}$ heteroaryl;

n is an integer having a value of 1 to 13; and m is an integer having a value of 1 to 13, or a pharmaceutically acceptable salt thereof.

The person skilled in the art would clearly recognize that compounds of formulas (IIa) and (IIb) are tautomers and that they may coexist at equilibrium. Under certain circumstances one of them may be more stable and therefore the equilibrium may be accordingly shifted towards this tautomer. Under other particular circumstances it may be possible that only one of the tautomers is substantially present. It will also be understood that the present invention also covers any other tautomers or isomers of the compounds of formulas (IIa) and (IIb).

In accordance with another aspect of the present invention there is provided compounds of formula (IIIa) or (IIIb) or stereoisomer or atropisomer thereof:

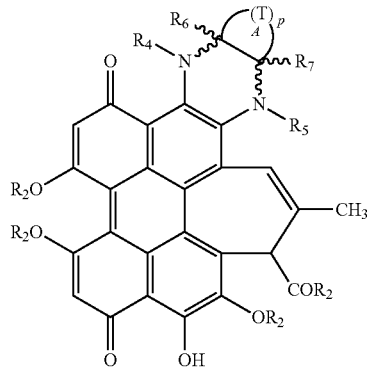

(IIIa)

-continued

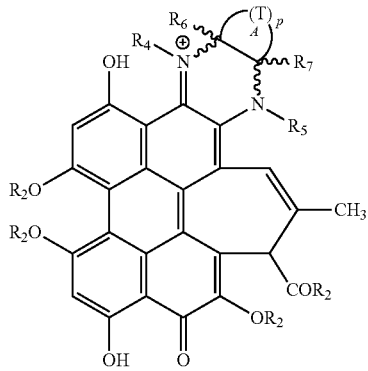

(IIIb)

wherein

T is a $C_1$-$C_4$ alkylenyl, $C_2$-$C_4$ alkenylenyl, $C_1$-$C_4$ heteroalkylenyl, $C_2$-$C_4$ heteroalkenylenyl, or combinations thereof;

$R_4$ and $R_5$ are independently hydrogen, deuterium, hydroxy, oxygen, halogen, $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, $C_1$-$C_{12}$ heteroaryl, —COR$_1$, —(CH$_2$)$_m$OR$_1$, —CO$_2$H, —CO$_2$R$_1$, —C(O)N(R$_1$)$_2$, —C(O)NH(R$_1$), —C(O)NH$_2$ or an amino suitable protecting group, said $C_1$-$C_4$ alkylenyl, $C_2$-$C_4$ alkenylenyl, $C_1$-$C_4$ heteroalkylenyl, $C_2$-$C_4$ heteroalkenylenyl, $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl being unsubstituted or substituted with at least one substituent selected from the group consisting of a halogen atom, hydroxy, carboxy, thiol, azide, nitro, $C_1$-$C_8$ deuterated alkyl group comprising at least one deuterated atom, —COH, —COR$_1$, —(CH$_2$)$_m$OR$_1$, —CO$_2$H, —CO$_2$R$_1$, —C(O)N(R$_1$)$_2$, —C(O)NH(R$_1$), —C(O)NH$_2$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl and $C_1$-$C_{12}$ heteroaryl;

$R_1$ is a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

each $R_2$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

p is an integer having a value of 0 to 8, and when p has a value of 1 to 8, ring A is saturated, or unsaturated and having at least one double bond, said ring A being unsubstituted or substituted with at least one substituent selected from the group consisting of a halogen atom, hydroxy, carboxy, thiol, azide, nitro, deuterium atom, $C_1$-$C_8$ deuterated alkyl group comprising at least one deuterated atom, —COH, NOH, —COR$_1$, —(CH$_2$)$_m$OR$_1$, —CO$_2$H, —CO$_2$R$_1$, —CON(R$_6$)$_2$, —C(O)NH(R$_1$), —C(O)NH$_2$, $C_1$-$C_8$ alkyl, $C_2$-$C_8$ alkenyl, $C_2$-$C_8$ alkynyl, $C_1$-$C_8$ alkoxy, $C_1$-$C_8$ thioalkoxy, $C_1$-$C_8$ alkylamino, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, $C_1$-$C_{12}$ heteroaryl, $C_1$-$C_8$ azaalkyl having at least one nitrogen atom, $C_6$-$C_{12}$ azaaralkyl having at least one nitrogen atom, $C_1$-$C_8$ haloalkyl having at least one halogen atom, a sugar (such as glucose, galactose, fucose, xylose, sialic acid, mannose, N-acetyl glucose amine, N-acetyl galactose amine, disaccharides, trisaccharides or derivatives thereof)

each $R_6$ is independently hydrogen, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, or an amino acid residue such as lysine, tryptophan, methionine, phenylalaine, threoine, valine, leucine, isolucine, arginine, tyrosine, glycine, serine, glutamic acid, aspartic acid, cystine, histidine, proline, alanine or derivatives thereof; and each $R_7$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl, or a pharmaceutically acceptable salt thereof.

The person skilled in the art would clearly recognize that compounds of formulas (IIIa) and (IIIb) are tautomers and that they may coexist at equilibrium. Under certain circumstances one of them may be more stable and therefore the equilibrium may be accordingly shifted towards this tautomer. Under other particular circumstances it may be possible that only one of the tautomers is substantially present. It will also be understood that the present invention also covers any other tautomers or isomers of the compounds of formulas (IIIc) and (IIIb).

In accordance with another aspect of the present invention there is provided compounds of formula (VIIa) or (VIIb) or stereoisomer or atropisomer thereof:

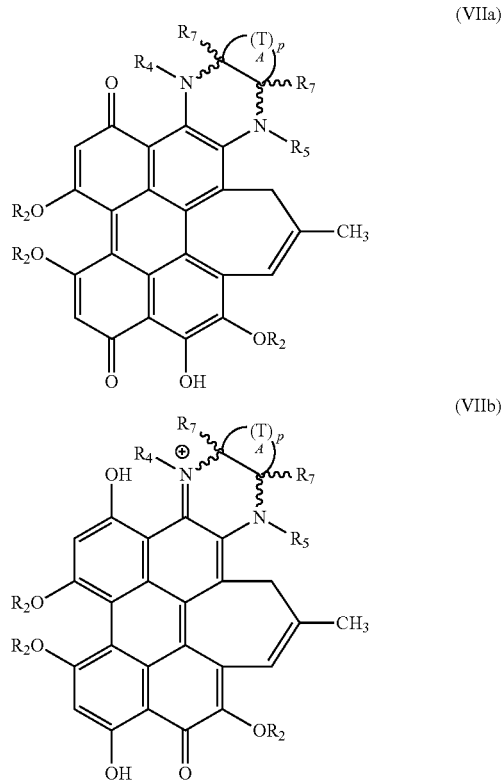

wherein

T is a $C_1$-$C_4$ alkylenyl, $C_2$-$C_4$ alkenylenyl, $C_1$-$C_4$ heteroalkylenyl, $C_2$-$C_4$ heteroalkenylenyl, or combinations thereof;

$R_4$ and $R_5$ are independently hydrogen, deuterium, hydroxy, oxygen, halogen, $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, $C_1$-$C_{12}$ heteroaryl, —$COR_1$, —$(CH_2)_mOR_1$, —$CO_2H$, —$CO_2R_1$, —$C(O)N(R_1)_2$, —$C(O)NH(R_1)$, —$C(O)NH_2$ or an amino suitable protecting group, said $C_1$-$C_4$ alkylenyl, $C_2$-$C_4$ alkenylenyl, $C_1$-$C_4$ heteroalkylenyl, $C_2$-$C_4$ heteroalkenylenyl, $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl being unsubstituted or substituted with at least one substituent selected from the group consisting of a halogen atom, hydroxy, carboxy, thiol, azide, nitro, $C_1$-$C_8$ deuterated alkyl group comprising at least one deuterated atom, —COH, —$COR_1$, —$(CH_2)_mOR_1$, —$CO_2H$, —$CO_2R_1$, —$C(O)N(R_1)_2$, —$C(O)NH(R_1)$, —$C(O)NH_2$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl and $C_1$-$C_{12}$ heteroaryl;

$R_1$ is a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

each $R_2$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

p is an integer having a value of 0 to 8, and when p has a value of 1 to 8, ring A is saturated, or unsaturated and having at least one double bond, said ring A being unsubstituted or substituted with at least one substituent selected from the group consisting of a halogen atom, hydroxy, carboxy, thiol, azide, nitro, deuterium atom, $C_1$-$C_8$ deuterated alkyl group comprising at least one deuterated atom, —COH, NOH, —$COR_1$, —$(CH_2)_mOR_1$, —$CO_2H$, —$CO_2R_1$, —$CON(R_6)_2$, —$C(O)NH(R_1)$, —$C(O)NH_2$, $C_1$-$C_8$ alkyl, $C_2$-$C_8$ alkenyl, $C_2$-$C_8$ alkynyl, $C_1$-$C_8$ alkoxy, $C_1$-$C_8$ thioalkoxy, $C_1$-$C_8$ alkylamino, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, $C_1$-$C_{12}$ heteroaryl, $C_1$-$C_8$ azaalkyl having at least one nitrogen atom, $C_6$-$C_{12}$ azaaralkyl having at least one nitrogen atom, $C_1$-$C_8$ haloalkyl having at least one halogen atom, a sugar (such as glucose, galactose, fucose, xylose, sialic acid, mannose, N-acetyl glucose amine, N-acetyl galactose amine, disaccharides, trisaccharides or derivatives thereof)

each $R_6$ is independently hydrogen, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, or an amino acid residue such as lysine, tryptophan, methionine, phenylalaine, threoine, valine, leucine, isolucine, arginine, tyrosine, glycine, serine, glutamic acid, aspartic acid, cystine, histidine, proline, alanine or derivatives thereof; and each $R_7$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl, or a pharmaceutically acceptable salt thereof.

The person skilled in the art would clearly recognize that compounds of formulas (VIIa) and (VIIb) are tautomers and that they may coexist at equilibrium. Under certain circumstances one of them may be more stable and therefore the equilibrium may be accordingly shifted towards this tautomer. Under other particular circumstances it may be possible that only one of the tautomers is substantially present. It will also be understood that the present invention also covers any other tautomers or isomers of the compounds of formulas (VIIa) and (VIIb).

It has been found that the compounds of the present invention have an improved photodynamic activity as compared with previously known compounds. As example, they have an enhanced photodynamic activity as compared to hypocrellin A or hypocrellin B. Moreover, the compounds of the present invention have a considerably enhanced photoresponse in the photodynamic window (red absorption). These compounds have also demonstrated a low toxicity.

It has also been found that the compounds of the present invention, which have a particular chromosphere (chromophore) or olefinic conjugation system permitting to obtain extended aromaticity, have an increased absorption of light in the range of 600-700 nm.

In the compounds of formula (Ia), (Ib), (IIa) or (IIb), Z is preferably —$CH_2$— and n has preferably a value of 3. X is preferably a methyl group. Y is also preferably a methyl group. $R_1$ is preferably hydrogen atom. Preferably, each $R_2$ is a methyl group.

In the compounds of formula (IIIa), (IIIb), (VIIa) or (VIIb), each $R_7$ is preferably a hydrogen atom. T is preferably —$CH_2$—. Preferably, p has a value of 4, so that ring A is a six-membered ring. Each $R_2$ is preferably a methyl group. $R_4$, $R_5$ and each $R_7$ preferably represent a hydrogen atom.

The term "alkyl" as used herein refers to linear or branched radicals. Examples of such radicals include, but are not limited to, methyl, ethyl, n-propyl, isopropyl, n-butyl, isobutyl, sec-butyl, tert-butyl, pentyl, iso-amyl, hexyl and the like.

The term "alkenyl" as used herein refers to linear or branched radicals having at least one carbon-carbon double bond in a radical. Examples of alkenyl radicals include, but are not limited to, ethenyl, propenyl, allyl, propenyl, butenyl and 4-methylbutenyl. The term "alkenyl" include radicals having "cis" and "trans" orientations, or alternatively, "E" and "Z" orientations.

The term "alkynyl" as used herein refers to linear or branched radicals. Examples of such radicals include, but are not limited to, propargyl, butynyl, and the like.

The term "cycloalkyl" as used herein refers to saturated carbocyclic radicals. Examples of such radicals include cyclopropyl, cyclobutyl, cyclopentyl and cyclohexyl. The term "cycloalkyl" additionally encompasses spiro systems wherein the cycloalkyl ring has a carbon ring atom in common with the seven-membered heterocyclic ring of the benzothiepene.

The term "cycloalkenyl" as used herein refers to unsaturated carbocyclic radicals having at least one double bond. Cycloalkenyl radicals that are partially unsaturated carbocyclic radicals that contain two double bonds (that may or may not be conjugated) can be called "cycloalkyldienyl". Examples of cycloalkenyl radicals includes, but is not limited to, cyclobutenyl, cyclopentenyl and cyclohexenyl.

The terms "halo" and "halogen" as used herein refer to halogen atoms such as fluorine, chlorine, bromine or iodine. The term "haloalkyl" includes radicals wherein any one or more of the alkyl carbon atoms is substituted with a halogen atom. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same or different halogen atoms. Examples of haloalkyl radicals include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" includes alkyl radicals having all hydrogen atoms replaced with fluoro atoms. Examples include trifluoromethyl and pentafluoroethyl.

The term "aryl" as used herein refers to a carbocyclic aromatic system containing one or more rings wherein such rings may be attached together in a pendent manner or may be fused. The term "aryl" includes, but is not limited to, aromatic radicals such as cyclopentodienyl phenyl, naphthyl, tetrahydronaphthyl, indanyl, biphenyl, and anthracenyl.

The term "heterocyclyl" as used herein refers to saturated, partially saturated and unsaturated heteroatom-containing ring-shaped radicals, where the heteroatoms may be nitrogen, sulfur, oxygen or combinations thereof. Preferred heterocyclyls include, but are not limited to, 3-10 membered ring heterocyclyl, particularly 5-8 membered ring heterocyclyl. Examples of saturated heterocyclic radicals include saturated 3 to 6-membered heteromonocyclic groups containing 1 to 4 nitrogen atoms (e.g., pyrrolidinyl, imidazolidinyl, piperidino, piperazinyl); saturated 3 to 6-membered heteromonocyclic groups containing from 1 to 2 oxygen atoms and from 1 to 3 nitrogen atoms (e.g., morpholinyl); saturated 3 to 6-membered heteromonocyclic groups containing 1 to 2 sulfur atoms and 1 to 3 nitrogen atoms (e.g., thiazolidinyl). Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl groups containing 1 to 4 nitrogen atoms, for example, pyrrolinyl, imidazolyl, pyrazolyl, 2-pyridyl, 3-pyridyl, 4-pyridyl, pyrimidyl, pyrazinyl, pyridazinyl, triazolyl (e.g., 4H-1,2,4-triazolyl, 1H-1,2,3-triazolyl, 2H-1,2,3-triazolyl); unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl); unsaturated 3 to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, isoxazolyl, oxadiazolyl (e.g., 1,2,4-oxadiazolyl, 1,3,4-oxadiazolyl, 1,2,5-oxadiazolyl); unsaturated condensed heterocyclic groups containing 1 to 2 oxygen atoms and 1 to 3 nitrogen atoms (e.g., benzoxazolyl, benzoxadiazolyl); unsaturated 5 to 6-membered heteromonocyclic groups containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl); unsaturated condensed heterocyclic groups containing 1 to 2 sulfur atoms and 1 to 3 nitrogen atoms (e.g., benzothiazolyl, benzothiadiazolyl) and the like. The term also includes radicals where heterocyclic radicals are fused with aryl radicals. Examples of such fused bicyclic radicals include benzofuran, benzothiophene, and the like.

"Heteroaryl" radicals can include, but are not limited to, fused or unfused radicals, particularly 3-10 membered fused or unfused radicals. Preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, furyl, and pyrazinyl. More preferred heteroaryl radicals are 5- or 6-membered heteroaryl, containing one or two heteroatoms selected from sulfur, nitrogen and oxygen such as thienyl, furanyl, thiazolyl, imidazolyl, pyrazolyl, isoxazolyl, isothiazolyl, pyridyl, piperidinyl or pyrazinyl. The term "heteroaryl" includes, but is not limited to, a fully unsaturated heterocyclyl. The term "heteroaryl" includes all positional isomers.

In either the "heterocyclyl" or the "heteroaryl" radical, the point of attachment to the molecule of interest can be at the heteroatom or elsewhere within the ring.

The term "aralkyl" as used herein refers to aryl-substituted alkyl radicals. Examples of such radicals include, but are not limited to, benzyl, diphenylmethyl, phenylethyl, triphenylmethyl, diphenylethyl.

The term "alkylenyl" as used herein refers to a straight or branched, divalent, saturated aliphatic chain carbon atoms. Such a term includes, but is not limited to, methylenyl, 1,1- ethylenyl, 1,2-ethylenyl, propylenyl, isopropylenyl, butylenyl, isobutylenyl, t-butylenyl, pentylenyl, isopentylenyl, hexylenyl, octylenyl, 3-methyloctylenyl, decylenyl.

The term "alkenylenyl" as used herein refers to linear or branched radicals having at least one double bond, and having attachment points for two or more covalent bonds. Examples of such radicals include, but are not limited to, 1,1-vinylidene ($CH_2$=C), 1,2-vinylidene (—CH=CH—), —CH=CH—$CH_2$—, and —CH=CH—CH=CH—.

The term "heteroalkylenyl," as used herein refers to a divalent group of atoms derived from a saturated straight or branched chain containing one or two heteroatoms independently selected from the group consisting of nitrogen, oxygen, and sulfur, wherein the remaining atoms are carbon. The heteroalkylenyl groups of the present invention can be attached to the parent molecular moiety through the carbon atoms or the heteroatoms in the chain.

The term "heteroalkenylenyl," as used herein refers to a divalent group of atoms derived from a straight or branched chain containing at least one carbon-carbon double bond that contains one or two heteroatoms independently selected from the group consisting of nitrogen, oxygen, and sulfur, wherein the remaining atoms are carbon. The heteroalkenylenyl groups of the present invention can be attached to the parent molecular moiety through the carbon atoms or the heteroatoms in the chain.

The term "atropisomer" as used herein refers to a stereoisomer where the element of chirality is located on a molecular plane or axis.

The expression "an amino suitable protecting group" as used herein refers to a protecting group that the person skilled would consider as effective for protecting an amino group. In a non-limitative manner, such a group can be one as defined in "Protective Groups in Organic Synthesis" by Greene, T.W; Wuts P.G.M; John Wiley and Sons, New York, Third Edition, 1999 on pages 494-653, which is hereby incorporated by reference.

The compounds of the present invention can be used as photosensitizers and/or sonosensitizers in a photodynamic and/or sonodynamic therapy. They can also be used for generating singlet oxygen and/or super oxide anion, when activated by light.

The compounds of the present invention can also be used for treating or detecting a target in a subject. The target can be a tissue, diseased tissue or a microorganism.

The tissue can be an epithelium, a connective tissue, muscle tissue and nervous tissue. The diseased tissue can be a lesion in a vascular system, a diseased bone marrow, a pre-cancerous lesion, a skin disease, diseased cells in which the disease is one of an autoimmune and an inflammatory disease. The diseased tissue may also be a hyperproliferative tissue.

The hyperproliferative tissue can be an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumors of a lung, a skin tumor, a nonsolid tumor and malignant cells of one of a hematopoietic tissue and a lymphoid tissue.

The skin disease can be actinic keratosis, acne, psoriasis or eczema.

The microorganism target can be bacteria, viruses, fungi or protozoa.

The compounds of the present invention can be used in the preparation of a medicament for treating hyperproliferative tissue disorders or for labeling a target tissue in diagnostic imaging such as in radiology.

In accordance with another aspect of the invention there is provided a composition comprising a compound according to the present invention, and a pharmaceutically acceptable carrier.

The composition containing a compound as defined in the present invention may include a wide variety of additional components, including, for example, one or more of gases, gaseous precursors, liquids, oils, stabilizing materials, diagnostic agents, pharmaceutical acceptable carriers, photoactive agents, bioactive agents and/or a targeting agent.

The pharmaceutical acceptable carrier can be a preservative solution, a saline solution, an isotonic (about 0.9%) saline solution, or about a 5% albumin solution, suspension, sterile water, phosphate buffered saline, and the like. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The compositions may be sterilized by conventional sterilization techniques.

In accordance with the present invention, the compounds or compositions may be administered to the patient by any biologically suitable route. For example, they may be introduced into the patient by intravenous, subcutaneous, intraperitoneal, intrathecal, intraarterial, intravesical, intradermal, intramuscular, or intralymphatic routes. The compounds or compositions may be in solution, tablet, aerosol, or multiphase formulation forms. Liposomes, long-circulating liposomes, immunoliposomes, biodegradable microspheres, micelles, or the like may also be used as a carrier, vehicle, or delivery system. The invention should not be limited to any particular method of introducing the compounds into the patient.

In accordance with the present invention, a desirable compound is preferably one that is non-toxic (or of low toxicity) at high drug concentrations without activation, i.e., without light (also referred to as "dark"), and is toxic at low concentrations when light of the appropriate wavelength, is applied. As is recognized by those skilled in the art, the most desirable compounds are those that provide a wide range of non-toxic doses in an un-activated state, as this characteristic provides an increased safety factor for the patient.

The invention also comprises using the above-mentioned compounds that have anti-cancer and/or anti-viral activity, and enhancing the activity of these derivatives by photoactivating them. The invention also includes using these compounds and compositions to preferentially destroy or preferentially target cancer cells.

In accordance with another aspect of the invention there is provided a kit for treating hyperproliferative disorders comprising a compound according to the present invention and instructions concerning a method of photodynamic therapy.

In accordance with another aspect of the invention there is provided a method for carrying out a photodynamic therapy on a subject. The method comprises a) administering to the subject a compound according to the present invention and b) irradiating the subject with a light having a wavelength suitable for activating the compound (such as generating singlet oxygen and/or super oxide anion).

In accordance with another aspect of the invention there is provided a method for treating a target in a subject. The method comprises a) administering to the subject a compound according to the present invention and b) irradiating the subject with a light having a predetermined wavelength suitable for causing activation of the compound, thereby treating at least a part of the target. The target can be one as previously defined. The method can further comprise the step of allowing sufficient time for the compounds that is not associated to the target tissue to clear from non-target tissue of the subject prior to the step of irradiating. The compound is preferably conjugated to a targeting agent. The targeting agent can be an antibody or an antibody fragment that is specific in binding with the target. Alternatively, the targeting agent is a peptide that is specific in binding with the target. Preferably, the targeting agent is a liposomal preparation.

In accordance with another aspect of the invention there is provided a method of photodynamic therapy for treating hyperproliferative tissue in a subject. The method comprises a) administering to the subject a compound according to the present invention, and b) irradiating the subject with a light having a wavelength sufficient to activate the compound, thereby treating at least a part of the hyperproliferative tissue. Preferably, in step (a), the compound associates with said hyperproliferative tissue.

It will be appreciated that the method of treatment may also be carried out using ultrasounds for activating the compounds of the invention instead of light.

In accordance with another aspect of the invention there is provided a method for detecting the presence of a hyperproliferative tissue in a subject comprising: a) administering to the subject a compound according to the present invention; and b) visualizing the compound within the subject. In step (a), the compound preferably associates with said hyperproliferative tissue. Step (b) can be carried out by generating an MRI image of at least a part of the subject's body or by means of a fluorescence character of the compound (for example by using an optical imaging). Step (b) is preferably carried out by activating said compound with a light having a wavelength suitable for causing the compound to fluoresce.

In accordance with another aspect of the invention there is provided a method for detecting a target in a biological sample, comprising: a) adding to the biological sample a compound according to the present invention that binds to the target; and b) detecting the compound bound to the target. As example, microspheres coated or chemically bonded with compounds of the present invention can be used as biological tracers in such a method. These fluorescent microspheres can be used in regional blood flow studies in tissues and organs. In most cases the microspheres can be injected at desired locations in the circulatory system and eventually lodge in the capillaries, where they can later be counted in dissected tissue sections. The biological sample can be selected from the group consisting of blood, urine, saliva, tears, synovial fluid, sweat, interstitial fluid, sperm, cerebrospinal fluid, ascites fluid, tumor tissue, biopsy and circulating tumor cells.

In accordance with another aspect of the invention there is provided a method for detecting an infecting agent in a subject. The method comprises: a) conjugating a compound according to the present invention to a targeting agent specific for the infecting agent so as to from a conjugate; b) administering to the subject said conjugate; and c) visualizing said conjugate within the subject. Step (c) can be carried out by generating an MRI image of at least a part of the subject's body. Step (c) can also be carried out by activating said compound with a light having a wavelength suitable for causing the compound to fluoresce.

In accordance with another aspect of the invention there is provided a method for generating an image of a target in a subject. The method comprises a) administering to the subject a compound according to the present invention so as to associate said compound with at least a part of the subject; and b) generating an image of the part to which said compound has been associated. The image can be a nuclear imaging image.

In accordance with another aspect of the invention there is provided a method of labeling a target for diagnostic radiology, comprising: a) administering to a subject a plurality of molecules of a compound according to the present invention so as to associate at least a part of the molecules to the target; and b) allowing sufficient time for molecules that are not associated to the target to clear from non-target tissue of the subject, thereby distinguishing the target from non-target tissue in an MRI image of the subject.

In accordance with another aspect of the invention there is provided a method of photodynamic therapy for treating a hyperproliferative tissue in a subject, comprising: a) administering to the subject a compound according to the present invention so as to associate said compound with the hyperproliferative tissue; and b) irradiating the subject with light having a wavelength suitable for activating said compound, thereby treating at least a part of the hyperproliferative tissue. The compound can be administered preferably topically, to the mucosa, systemically, to the female genital tract or rectally.

In accordance with another aspect of the invention there is provided a method for treating a cell proliferative disorder, comprising administering to a subject in need thereof an effective amount of a compound according to the present invention, thereby treating said cell-proliferative disorder. The cell proliferative disorder can be cancer. The cell proliferation can be reduced, or cell death is induced.

In the methods the present invention, the subject can be an animal such as a mammal and preferably a human.

The term "administering" as used herein refers to action that results in exposing or contacting one or more compound of the present invention with a pre-determined cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a compound or composition composition of the present invention, e.g., by washing or irrigating the surgical site and/or the cells. Route of administration covers intra-venous, subcutaneous, intra-lymphatic, intra-peritonial, intra-vesical, intradermal, intra-muscular, intra-arterial, etc.

The terms "activation" and "activating" or similar terms, as used herein, refers to the use of light waves to make a compound or portion of a compound more chemically reactive. Any method for applying a light source to a perylenequinone derivative may be used in accordance with the present invention, e.g., direct application, illuminating endoscopy, etc. As example such an activation can generate singlet oxygen and/or super oxide anion.

The expression "hyperproliferative tissue" as used herein refers to a tissue such as psoriasis, cancer tumors, non-cancer tumors, atopical dermatitiis, plaques in blood vessels, age related macular degeneration, Actinic, vaginal warts, tissues to be treated including those of neck, bladder, head, brain, eye, ear etc.

The expression "treating" as used herein when referring to an hyperproliferative tissue means reducing the size of the tissue, eliminating the tissue or damaging at least a part of the tissue.

In accordance with another aspect of the invention there is provided a process for preparing a compound of formula (Ia) or (Ib), as previously defined. The process comprises:
  a) reacting a compound of formula (IVa) or (IVb) or a stereoisomer or atropisomer thereof:

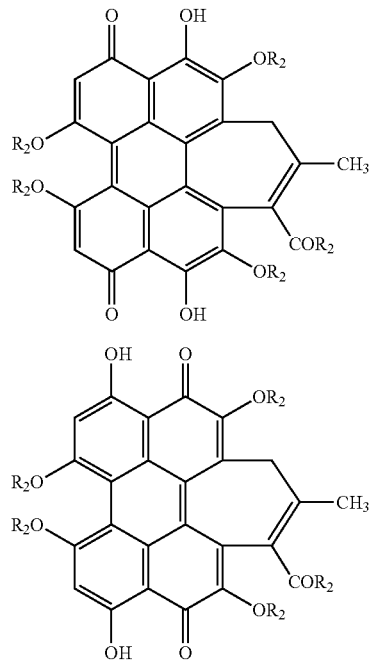

wherein
$R_2$ is as previously defined for formulas (Ia) and (Ib), with a compound of formula (V):

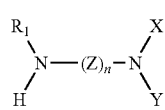

wherein
X, Y, Z, $R_1$ and n are as previously defined for formulas (Ia) and (Ib).

Step (a) can be carried out at a temperature of about 40 to about 100° C. Preferably, step (a) is carried out at a temperature of about 55 to about 59° C.

In accordance with another aspect of the invention, there is provided a process for preparing a compound of formula (IIa) or (IIb), as previously defined. The process comprises:
  a) reacting a compound of formula (IVa) or (IVb) or a stereoisomer or atropisomer thereof:

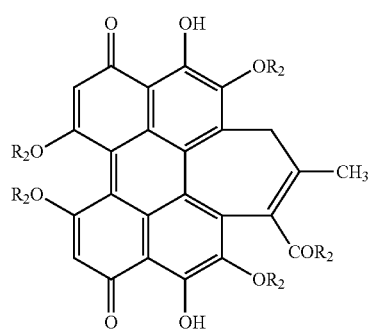

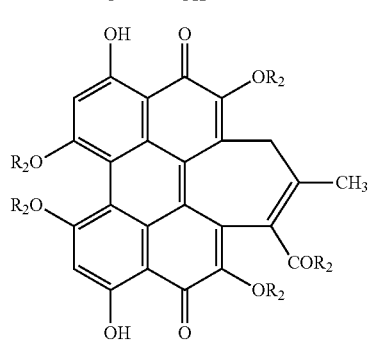

wherein
$R_2$ is as previously defined for formulas (IIa) and (IIb) with a compound of formula (V):

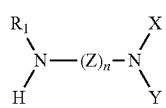

wherein
X, Y, Z, $R_1$ and n are as previously defined for formulas (IIa) or (IIb).

Step (a) can be carried out at a temperature of about 40 to about 100° C. Preferably, step (a) is carried out at a temperature of about 55 to about 59° C.

In accordance with another aspect of the invention, there is provided a process for preparing a compound of formula (IIIa), (IIIb) (VIIa) or (VIIb), as previously defined. The process comprises:
  a) reacting a compound of formula (IVa) or (IVb) or stereoisomer or atropisomer thereof:

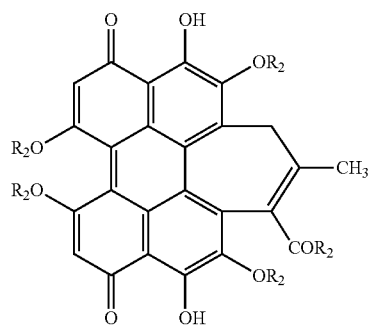

-continued

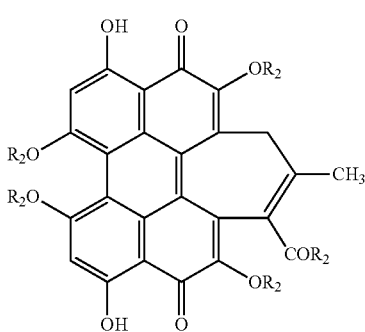

(IVb)

wherein
R$_2$ is as previously defined for formulas (IIIa) or (IIIb)
with a compound of formula (VI):

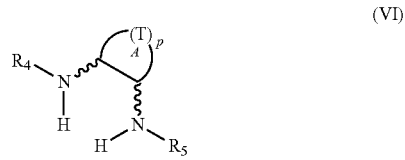

(VI)

wherein
T, R$_4$, R$_5$, and p are as previously defined for formulas (IIIa) or (IIIb).

Step (a) can be carried out at a temperature of about 40 to about 100° C. Preferably, step (a) is carried out at a temperature of about 55 to about 59° C.

BRIEF DESCRIPTION OF THE DRAWINGS

Further features and advantages of the present invention will become apparent from the following detailed description, taken in combination with the appended drawings, in which.

DETAILED DESCRIPTION OF PREFERRED EMBODIMENTS OF THE INVENTION

The following examples represent in a non-limitative, preferred embodiments of the present invention.

Specific examples of particular compounds of the present invention have been prepared as shown is schemes 1 and 2:
Scheme 1
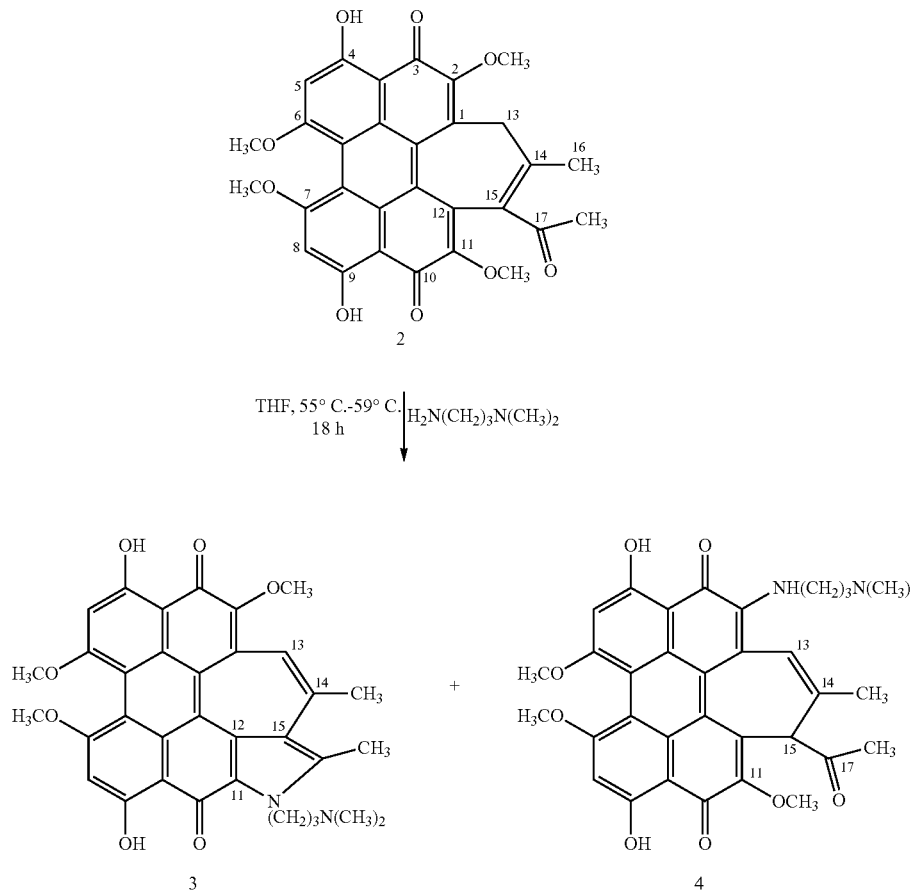
Scheme 2
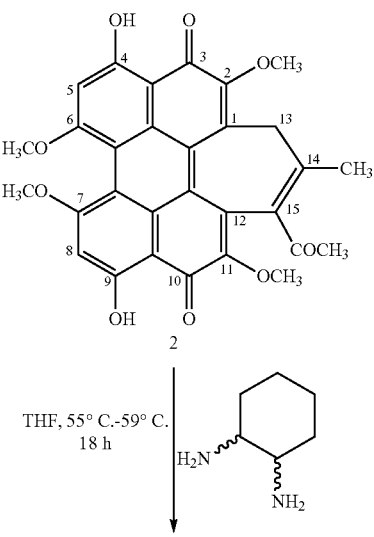

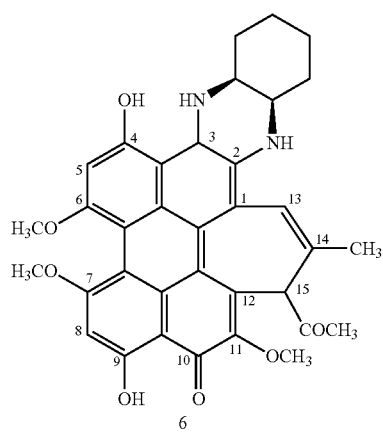

6

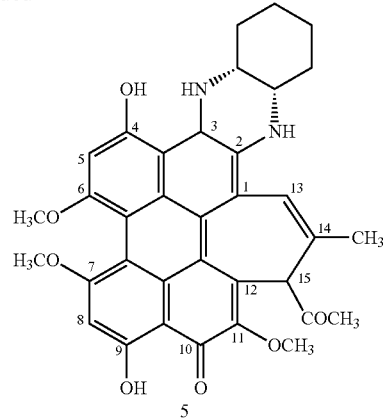

5

In Scheme 1, the amine used is a substituted aliphatic compound, and in Scheme 2, cis-1,2-diaminocyclohexane and trans 1,2-diaminocyclohexane derivatives are used. When comparing the $^1$H NMR data of these two compounds (see the characterization of these compounds) with the parent hypocrellin B (2) it can be noted that both the compounds (3) and (4) have three methoxy groups intact, the two methoxy groups at C-6 and C-7 position of the molecules are intact, that means the substitution has taken place either at the C-2-methoxy or at C-11-methoxy group of hypocrellin B (2). Substitution of C-11-methoxy group with amine, which forms an imine with the carbonyl group at the C-17 position, thereby forming a N-substituted five-member ring with C-11 and C-17 cyclization. To provide the stability to the seven-member ring, and the stability of the molecule the double bond migration takes place from 14-carbon and 15-carbon to 13-carbon and 14-carbon. This is evident from downfield shift of 13-H to δ 7.20 singlet for one proton from δ 3.21 and δ 4.02 (in CDCl$_3$) double doublet for two proton of 13-H in the parent hypocrellin B (2) (see the characterization of these compounds).

Figure 11:
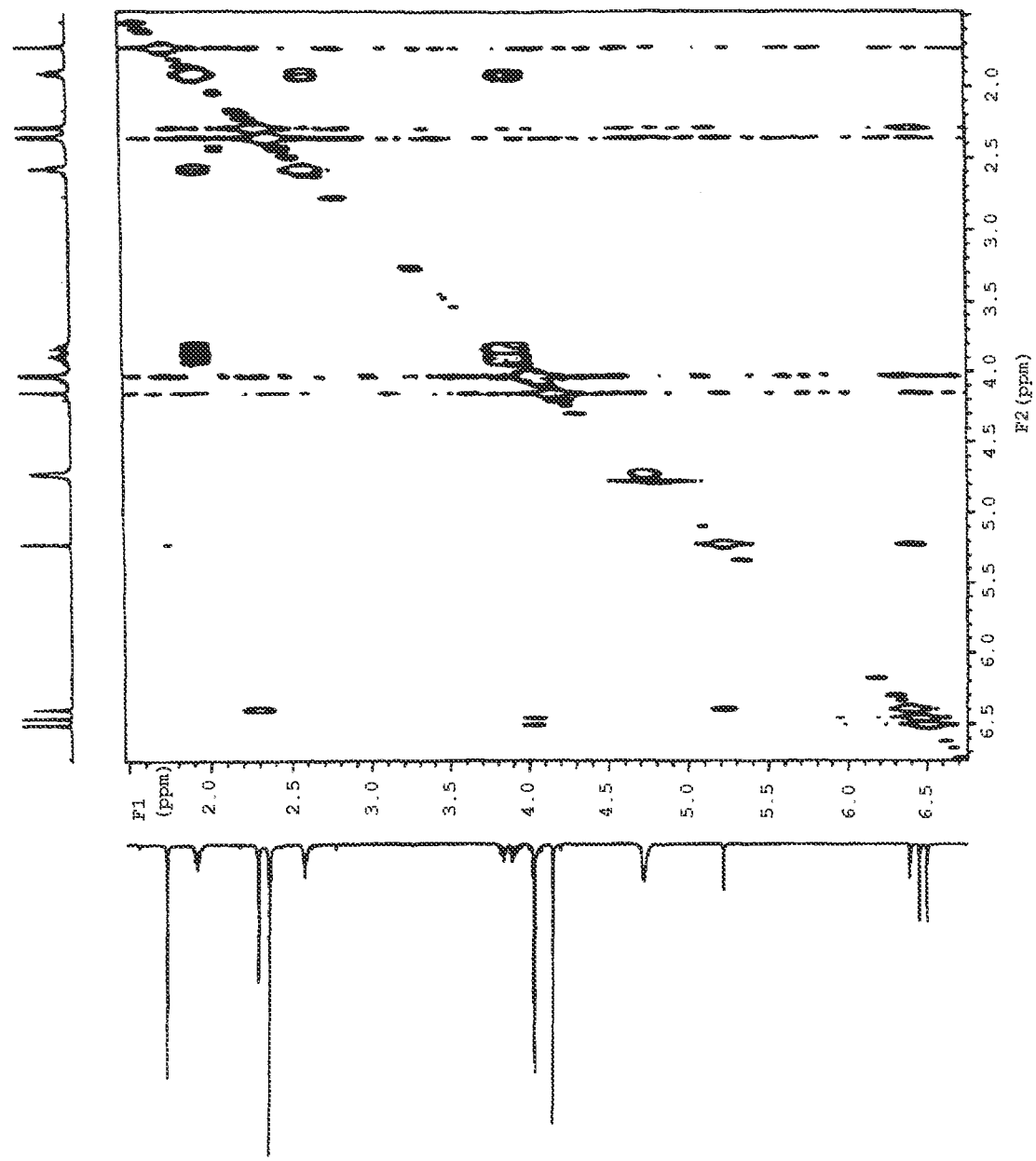
FIG. 11 is a COSY NMR spectra of a compound according to a preferred embodiment of the invention.
Figure 12:
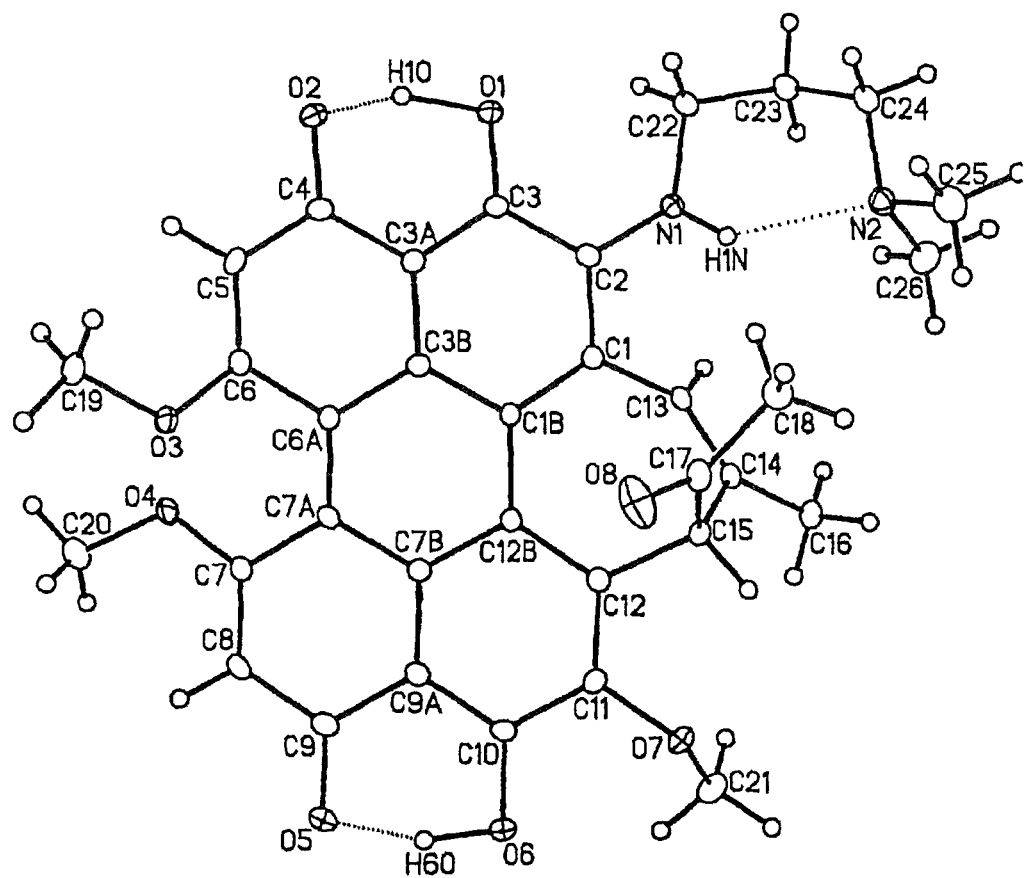
FIG. 12 is a X-ray diagram of a compound according to a preferred embodiment of the invention.

For the compound (4), it was found that in the aprotic solvent reaction conditions, the nucleophilic substitution with amino group takes place at the 2-methoxy group (at position 2) and in order to attain the stability in the seven member ring of the parent molecule and also to attain the extended aromaticity, the double bond migration takes place from 14 carbon and 15 carbon to 13 carbon and 14 carbon. In other words, the 13-H-Cyclohepta (ghi) structure of the parent hypocrellin B (2) has changed to 15-H-cyclohepta (ghi) structure. As evidenced from the downfield shift of 13-H to δ 5.15, singlet for one proton from δ 3.21 and δ 4.02 (in CDCl$_3$) double doublet for two proton of 13-H in the parent hypocrellin B (2) (see the characterization of these compounds). While the aromatic region has one singlet at δ 6.40 for one proton, which is for 15-H which was absent in their parent compound because of the 14 carbon and 15-carbon double bond. Detailed COSY NMR was carried on this molecule, which indicated that the proton at δ 6.40 showed intraction with the methyl group at C-14 δ 2.40, thereby indicating that these two protons are in close proximity and in the same plane (FIG. 11). To confirm these physical observations on compound (4), an X-ray crystallography was conducted on the single crystal of compound (4) (FIG. 12). The X-ray diagram of compound (4) (FIG. 12) showed that the 15 carbon has one proton, which is in the same plane as 14-C methyl, and the 13-carbon has one proton. The 15-C is in the sp$^3$ hybridization while the 13-C is in sp$^2$ hybridization, confirming that the 13-carbon is in double bond with 14-carbon. The bond distance between 13-C and 14-C is 1.328 Å which confirms the double bond. On the basis of $^1$H NMR, COSY NMR and X-ray crystallographic studies, it was confirmed that the nucleophillic substitution by an amine takes place at C-2 methoxy and thereby leading to 15-H cyclohepta (ghi) perylenequinonoid ring system instead of the 13-H cyclohepta (ghi) perylenequinonoid ring system which is an unexpected result in these types of reactions.

Compounds (4) and (5) were studied for their photo physical properties using various physical methods. Without wishing to be bound by any theory, it is believed that this unexpected shift of double bond position can potentially be responsible for at least a part of the extended light absorption and photo toxicity in killing the tumors effectively.

The compounds of the invention may also exist as atropisomers as shown below.

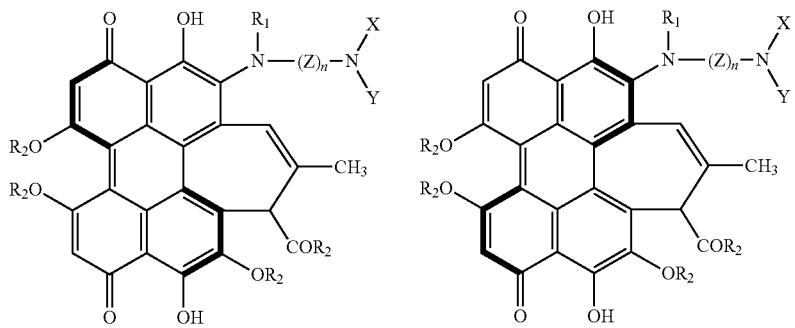

Atropisomers of (Ia)

-continued

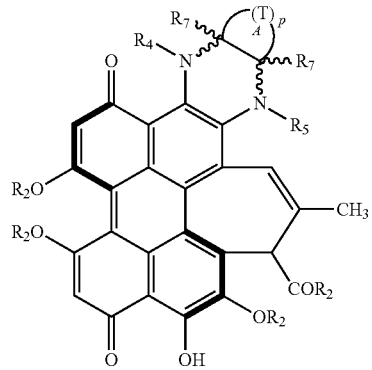 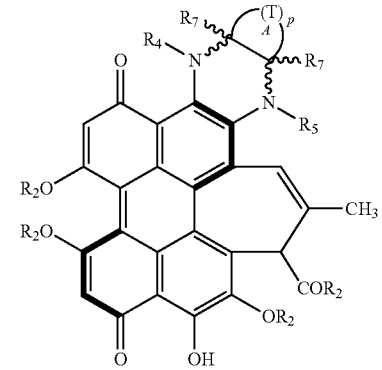

Atropisomers of (IIIa)

The compounds of the present invention can be used as photosensitizers in a photodynamic therapy. As will be shown below, the compounds, when activated by light, are capable of generating singlet oxygen and/or super oxide anion. The compounds can be activated by light of a suitable wavelength. The wavelength is preferably in the range of 600-700 nm. Light in this rregion of the spectrum advantageously exhibits a better penetration in biological tissue than light a lower wavelegnths such as those used to excite the parent compound hypocrellin.

Light sources used to activate the compounds of the invention such as fiber catheters are well known in the art.

The compounds of the present invention can also be used as sonosensitizers in a sonodynamic therapy (SDT). The compounds of the present invention exhibit excellent sonodynamic activity in a frequency range from about 1 MHz to about 3 MHz. The treatment can be delivered by subjecting a desired region (a target) in a subject, such as an organ or part of an organ to ultrasounds using a pre-determined duty cycle. The parameters of the duty cycle includes the power level as well as the duration of the cycle. Typical power levels will vary from 1 milli-watt to 10 watt for typical duration of 10 seconds to 10 minutes. The cycle also typicaly comprises an "off" period of 10 seconds to 10 minutes. The parameters of the duty cycle as well as the choice of the frequency can be determined by practioners in the field of sonodynamic therapy. Therapeutic ultrasound devices are well known in the art.

The compounds of the present invention can be used for treating a target in a subject. By target it is meant any part of the body of a subject. Thus the target can be any tissue such as epithelium, connective tissue, muscle tissue and nervous tissue. The tissue can be a diseased tissue. In particular the tissue can be a hyperproliferative tissue such as a cancerous tissue which can be but is not limited to an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumors of a lung, a skin tumor, a nonsolid tumor and malignant cells of one of a hematopoietic tissue and a lymphoid tissue.

The diseased tissue can also be lesions in a vascular system, a diseased bone marrow, a pre-cancerous lesion, a skin disease, diseased cells in which the disease is one of an autoimmune and an inflammatory disease. Examples of skin diseases amenable to be treated by the compounds and method of the invention include actinic keratosis, acne, psoriasis, eczema and the like.

Furthermore the target may also be a microorganism such as bacteria, viruses, fungi and protozoa that can cause infection in a subject.

In accordance with another aspect of the invention there is provided a method for carrying out a photodynamic therapy on a subject. The method comprises administering to the subject a compound according to the present invention in an amount sufficient to sensitize a desired region (target) in the individual to light and irradiating the subject with a light having a wavelength suitable for activating the compound (such as by generating singlet oxygen and/or super oxide anion).

By "an amount sufficient to sensitize a region" (an organ or part of an organ for example) to light it is meant that the compound should administered at a concentration sufficient to cause the desired effect when the target is irradiated. Such a concentration can be determined by medical practitioners. Typical doses for systemic administration are between about 1-15 mg/Kg. Typical doses for topical administration is about 0.01 to 10 mg/cm$^2$.

It will be appreciated that the therapy can be effected by either providing a compound of the invention directly to a target in a subject or by allowing the compound to reach the target and irradiating the target thereby treating at least a part of the target.

The method can further comprise the step of allowing sufficient time for the compounds that is not associated to the target tissue to clear from non-target tissue of the subject prior to the step of irradiating.

It will be appreciated that the steps of the method described above for photodynamic therapy can also be applied to sonodynamic therapy wherein the activation of the compound is achieved using ultrasounds.

The compounds of the present invention may be conjugated to a targeting agent. The targeting agent can be an antibody or an antibody fragment that is specific in binding with the target. Alternatively, the targeting agent is a peptide that is specific in binding with the target. The targeting agent may also be a liposomal preparation incorporating a compound of the invention. The liposomal preparation may comprise molecules, such as antibodies, capable of helping or enhancing specific targeting.

In accordance with another aspect of the invention there is provided a composition comprising a compound according to the present invention, and a pharmaceutically acceptable carrier.

The pharmaceutical acceptable carrier can be a preservative solution, a saline solution, an isotonic (about 0.9%) saline solution, or about a 5% albumin solution, suspension, sterile water, phosphate buffered saline, and the like. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The composition may also comprise skin penetration enhancers. The optimal percentage of the compounds of the invention in each pharmaceutical formulation varies according to the formulation itself and the therapeutic effect desired in the specific pathologies and targets.

The amount of the compound presents in a target can be measured using its fluorescence characteristics. This advantageously enables the intensity/duration of the light or ultrasound activation to be adjusted accordingly.

The compositions may be sterilized by conventional sterilization techniques.

The composition containing a compound as defined in the present invention may include a wide variety of additional components, including, for example, one or more of gases, gaseous precursors, liquids, oils, stabilizing materials, diagnostic agents, photoactive agents, bioactive agents and/or a targeting agent.

Thus the compounds of the present invention can be used in the preparation of a medicament for used in photodynamic and sonodynamic therapies.

A desirable compound is preferably one that is non-toxic (or of low toxicity) at high drug concentrations without activation, i.e., without light (also referred to as "dark") and is toxic toward a desired target at low concentrations when light of the appropriate wavelength, is applied. As is recognized by those skilled in the art, the most desirable compounds are those that provide a wide range of non-toxic doses in an un-activated state, as this characteristic provides an increased safety factor for the patient.

The compounds or compositions may be administered to the patient by any biologically suitable route. For example, they may be introduced into the patient by intravenous, subcutaneous, intraperitoneal, intrathecal, intraarterial, intravesical, intradermal, intramuscular, topical, mucosal, rectal or intralymphatic routes. The compounds or compositions may be in solution, tablet, aerosol, or multi-phase formulation forms. Liposomes, long-circulating liposomes, immunoliposomes, biodegradable microspheres, micelles, or the like may also be used as a carrier, vehicle, or delivery system. The invention should not be limited to any particular method of introducing the compounds into the patient.

In another embodiment of the invention there is provided a kit for treating hyperproliferative disorders such as cancer comprising a compound according to the present invention and instructions concerning a method of photodynamic therapy and/or sonodynamic therapy.

The compounds of the present invention can also be used for cosmetic purposes such as body hair removal. In this case the compounds can be administered topically or systemically and the region of the skin from which it is desired to remove hair is irradiated.

In another aspect of the invention there is provided a method for detecting the presence of a target in a subject by administering to the subject a compound according to the present invention and visualizing the compound within the subject. The compound preferably associates with the target (using a targeting agent coupled to the compound for example) and can be detected by an appropriate imaging or detection method. Non limiting examples include MRI imaging, optical imaging, fluorescence detection of the compound by irradiating the subject with a wavelength capable of inducing the compound to fluoresce. The target may comprise a microorganism. The target to be detected may be in a biological sample.

Microspheres coated or chemically bonded with compounds of the present invention can also be used as biological tracers in such a method.

These fluorescent microspheres can be used in regional blood flow studies in tissues and organs. In most cases the microspheres can be injected at desired locations in the circulatory system and eventually lodge in the capillaries, where they can later be counted in dissected tissue sections. The biological sample can be selected from the group consisting of blood, urine, saliva, tears, synovial fluid, sweat, interstitial fluid, sperm, cerebrospinal fluid, ascites fluid, tumor tissue, biopsy and circulating tumor cells.

Many processes have been shown to be detectable by compounds similar to compounds of the present invention. Cell viability, cell proliferation and many important cell functions including apoptosis, cell adhesion, chemotaxis, multidrug resistance, endocytosis, secretion and signal transduction can be stimulated or monitored with various chemical and biological reagents. Many of these processes lead to changes in intracellular radicals, free ion concentrations or membrane potential that can be followed with appropriately responsive fluorescent reagents. For example, the compounds of the invention can be conjugated to antibodies specific for markers of cellular proliferation such as Bromo deoxyuridine (BrdU).

It will be appreciated that the compounds and methods of the present invention can be used to treat any animal and more particularly mammals including humans.

A new approach has thus been developed in order to overcome the limitations of the natural compounds or the hypocrellin derivatives previously known in the art. In particular, it has been found that by carrying out a nucleophillic substitution of the methoxy group on the carbon atom at position 2 of hypocrellin B, a migration of the olefinic double bond between positions 14 and 15 occurred. In fact, in the compounds derived from such a nucleophilic substitution there was no double bond between carbon atoms 14 and 15 as in the starting material (hypocrellin B). This double bond has migrated from between the carbon atoms 14 and 15 and is found in the obtained products between carbon atoms 13 and 14. It is believed, without wishing to be bound to such a theory, that such a particular configuration of the aromaticity may explain the enhanced photoactivity of the compounds of the present invention. Moreover, such a synthetic approach has permitted the discovery of these compounds having remarkably enhanced red absorption (photodynamic window), possessing higher photodynamic activity with minimum toxicity in the absence of light. Both in vitro and in vivo results obtained demonstrate that the above-mentioned compounds are effective and that they are superior to parent compounds hypocrellin A and B.

EXAMPLES

Example 1

Absorption and Fluorescence Spectra of Compounds (4) and (5)

Figure 1:
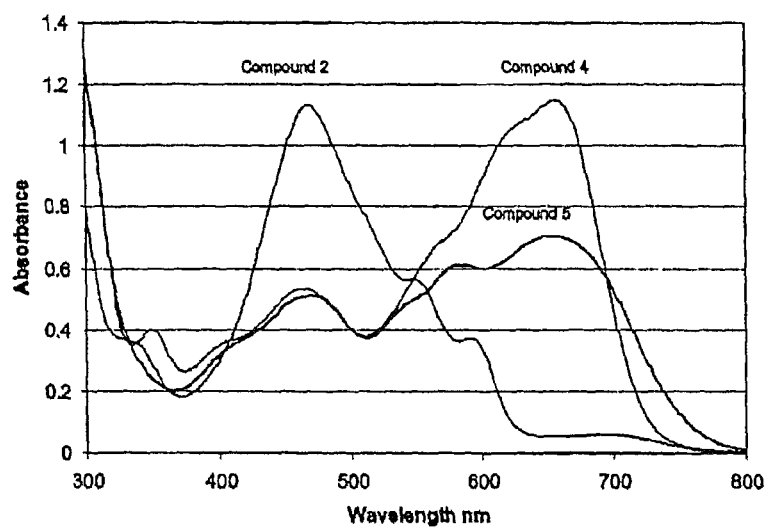
FIG. 1 is a UV-visible absorption spectra, recorded in DMSO (dimethylsulfoxide), of compounds according to a preferred embodiment of the invention.

The absorption spectra of compounds (4) and (5) recorded in DMSO are shown in FIG. 1 along with the parent compound (2). Based on the study of absorption spectra of hypocrellin B (2) (Diwu et al. *Sinica Sol. B* 18, 1993, 131), the shorter wavelength absorption bands are assigned to the π-π* transition, and the absorption bands at the longer wavelength is the relation to intermolecular charge transfer (ICT) which may take on some active role in the photodynamic activity of the molecule. From FIG. 1, the absorption at the longer wavelengths of compounds (4) and (5) has enhanced, as compared to the parent hypocrellin B (2). The maximum absorption of compounds (4) and (5) is around 600-700 nm in DMSO which helps in tissue penetration, while the parent compound hypocrellin (2) has maximum absorption at 580 nm in DMSO. When an electron donating group like 3-dimethylaminopropylamine is introduced in the quinonoid molecule, its interaction with the adjacent carbonyl group enhances the red shift in the absorption spectra, thereby leading to an extended red shift spectral region (photodynamic window) which is important for PDT.

Figure 2:
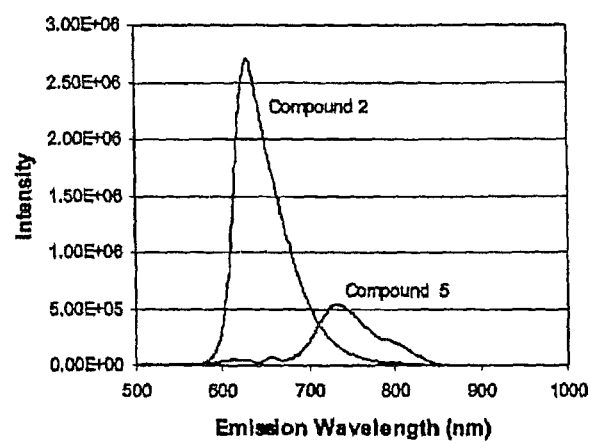
FIG. 2 shows the comparison between a fluorescence spectra of hypocrellin B in chloroform and a fluorescence spectra of a compound according to a preferred embodiment of the invention, in chloroform.

The fluorescence spectra of hypocrellin B (compound (2)) and compound (5) (in chloroform) are shown in FIG. 2. The introduction of the extra cyclic ring in compound (5) have shown a new fluorescent band at longer wavelength (around 725 nm), because of the intermolecular H-atom transfer process. The new florescent band is considered to be related to the ICT between the amino group and the quinine carbonyl group.

Example 2

Evidence for Generation of Singlet Oxygen

Reactive oxygen spices generated can be measured using various optical assays and EPR method.

Optical assay (Mothilal K. et al. *J Photochem. Photobiol. Chem.*, 262, 2004, 9-16.)

Figure 3:
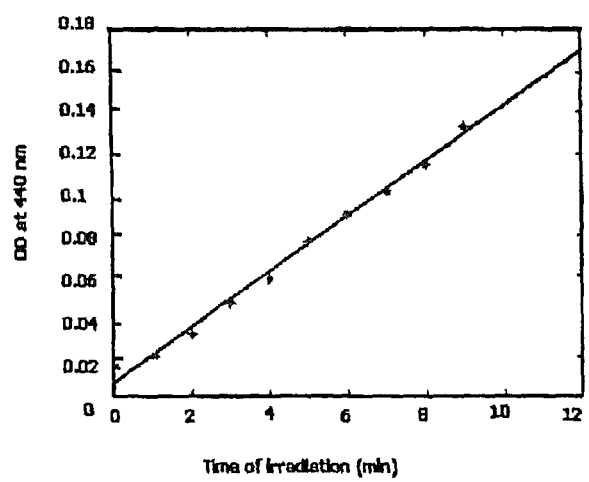
FIG. 3 is a plot showing the results obtained during an optical assay for singlet oxygen using the RNO(N,N-dimethylnitrosoaniline) bleaching method, which was carried out by irradiating a compound according to a preferred embodiment of the invention.

Optical assay for singlet oxygen was performed using RNO bleaching method (Mothilal K. et al. *J Photochem. Photobiol. Chem.*, 262, 2004, 9-16). The drug (1 mM) was irradiated in the presence of imidazole (10 mM) and RNO (50 mM) in phosphate buffer (pH 7.4), bleaching of RNO by singlet oxygen was followed spectrophotometrically at 440 nm. The interference of super oxide and hydrogen peroxide on RNO bleaching was removed by the addition of super oxide dismutase (SOD) and catalase, respectively. Bleaching of RNO as a function of time by compound is shown in FIG. 3.

EPR Spin Trapping Assay (Rajamanicakam, et al. *Biochim. Biophys. Acta* 1622 (2), 2003, 65-72.)

Due to the broad absorption of the compound in the visible region we use optical method for qualitative assessment rather than quantitative. The generation ROS is further confirmed by EPR method. EPR spin trapping experiments were carried out using JEOL TES-TE 100 ESR spectrometer operating at X-band frequency with 100 kHz field modulation at room temperature.

The photo generation of singlet oxygen by drug in DMSO was also investigated by EPR measurement. 2,2,6,6-tetramethyl piperidinol (TEMPL) was used as a singlet oxygen trapper, by converting it to an EPR detectable nitroxide free radical, Air saturated reaction mixture (1 ml) containing 0.2M TEMPL and 1 mM of compound was irradiated and the increase in EPR signal intensity was followed as a function of irradiation time. (FIGS. 4 and 5).

Figure 4:
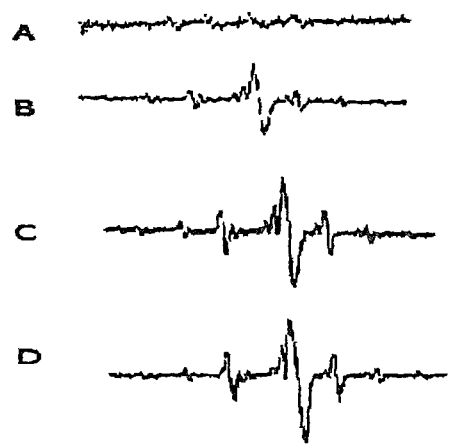
FIG. 4 is a EPR (Electron Paramagnetic Resonance) spectra of TEMPOL (4-hydroxy-2,2,6,6-tetramethyl piperidine-1-oxyl) generated during photoiridiation of a solution comprising DMSO, TEMPL (2,2,6,6-tetramethyl piperidinol) and a compound according to a preferred embodiment of the invention.
Figure 5:
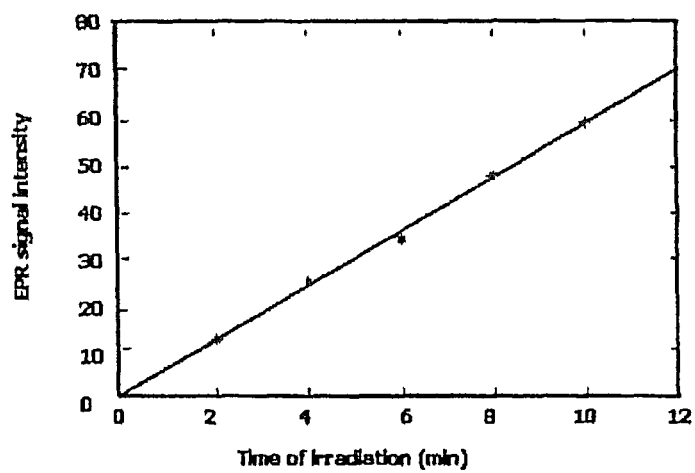
FIG. 5 is a plot showing an EPR signal intensity for singlet oxygen as a function of time of irradiation of a compound according to a preferred embodiment of the invention.

FIG. 4 shows the EPR spectra of TEMPOL generated during the photoirradiation of DMSO solution of compound (4) (1 mM) in the presence of TEMPL (20 mM) at 500K, (A) In the dark, (B) 4-minute irradiation, (C) 6-minute irradiation and (D) 10-minute irradiation. The spectrometer setting are the following: microwave power, 2 mW; modulation frequency, 100 kHz; modulation amplitude, 0.5; time constant, 0.1 s; scan rate, 4 minute; scan width, 200 G; receiver gain, 500; line width, 1.1. FIG. 5 is a plot showing the EPR signal intensity for singlet oxygen generation Vs time of irradiation of compound (4) in accordance with FIG. 4.

Example 3

Evidence for Generation of Super Oxide Anion

Optical Assay

Figure 6:
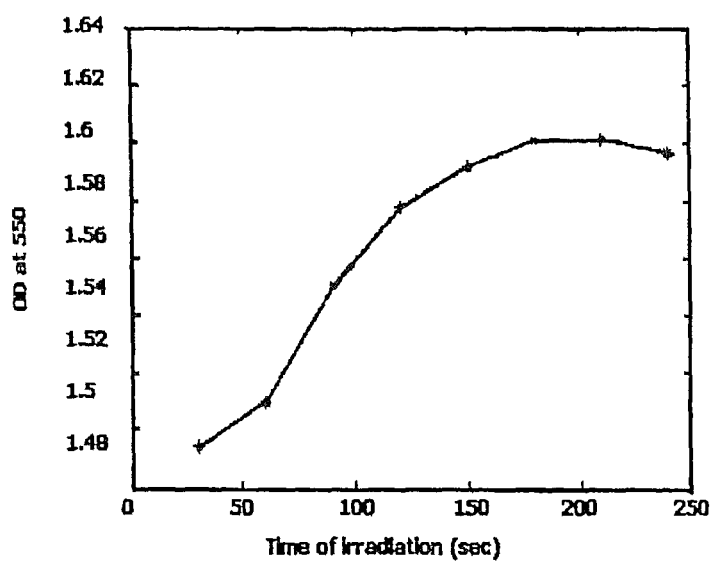
FIG. 6 is a curve representing the evolution of the 550 nm absorption peak of cytochrome c as a function of time during an optical assay for determining the presence of super oxide anion by illuminating a compound according to a preferred embodiment of the invention.

SOD inhibitable cytochrome c reduction method was used for super oxide detection. The drug (compound (4)) (1 mM) was illuminated in the presence of cytochrome c (40 µM) in 50 mM phosphate buffer (pH 7.4). The reaction was followed by observing the increase in 550 nm absorption peak of cytochrome c as a function of time (FIG. 6).

EPR Spin Trapping.

Figure 7:
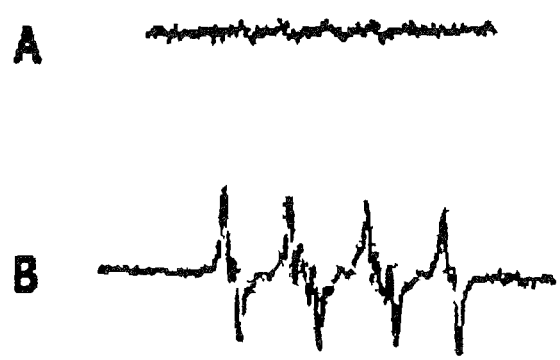
FIG. 7 represents an EPR spectra in the dark (A) and after four minutes of irradiation (B) of a solution comprising DMSO, DMPO (5,5-dimethyl-1-pyrroline-N-oxide) and a compound according to a preferred embodiment of the invention.

Photo generation of superoxide anion by drug was verified by EPR spin trapping technique. Solution of compound (4) (1 mM) and 5,5-dimethyl-1-pyrroline-N-oxide (DMPO) (100 mM) in DMSO were irradiated and a 12-line EPR spectrum characteristic of DMPO-super oxide adduct was obtained confirming the generation of super oxide (see FIG. 7). (A) represents the in the dark and (B) after 4-minute irradiation. The spectrometer settings were the following: microwave power, 2 mW; modulation frequency, 100 kHz; modulation amplitude, 0.5; time constant, 0.1 s; scan rate, 4 minute; scan width, 200 G; receiver gain, 500; line width, 1.1.

From these experimental results it was concluded that on irradiation the compounds of the present invention generates both singlet oxygen and superoxide anion.

Example 4

Dark Toxicity

EMT-6 cells in log phase growth were plated onto 35 mm dishes 24 hours prior to experimentation. Growth media was removed and replaced with media containing compounds (4) and (5) at the doses (0, 2.5 µM, 5 µM and 20 µM). The plates were then kept at 37° C. for 3 hours in the dark and then the cells were washed 2 times in PBS then trypsinized and re-plated at 200 cells/60 mm dish in normal RPMI growth media. The cells were allowed to grow for 7 days and then stained with Methylene Blue and the surviving colonies counted.

Example 5

Light Treatment

EMT-6 cells in log phase growth were plated onto 35 mm tissue culture dishes 24 hours prior to experimentation. Growth media was removed and replaced with media containing compounds (4) or (5) at the above doses—0, 2.5 µM, 5 µM and 20 µM (Initially, the drugs were dissolved in pure DMSO @ a concentration of 2 mM). They were diluted down to the appropriate concentrations in RPMI growth media. The plates were then kept at 37° C. for 3 hours in the dark and then the cells were washed 2 times in PBS and finally had 2 ml of RPMI added to each dish. Then, the dark toxicity samples were kept covered at room temperature for the equivalent time taken for light treatment of the other samples. Light treated samples were subjected to grades doses of light (0, 0.5, 1, 2.5 and 5 J/cm$^2$) from 635 nm laser with a fluency rate of 150 milli watts. The media was removed and the cells trypsinized and re-plated at 200 cells/60 mm dish in normal RPMI growth media. The cells were allowed to grow for 7 days and then stained with Methylene Blue and the surviving colonies counted.

Figure 8:
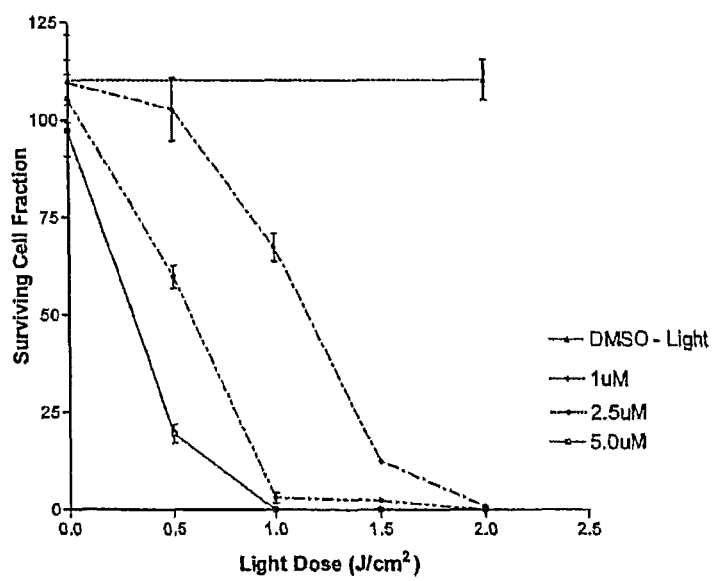
FIG. 8 is a graph showing the influence of a compound according to another preferred embodiment of the invention on EMT-6 cells, when the compound is submitted to a light treatment.
Figure 9:
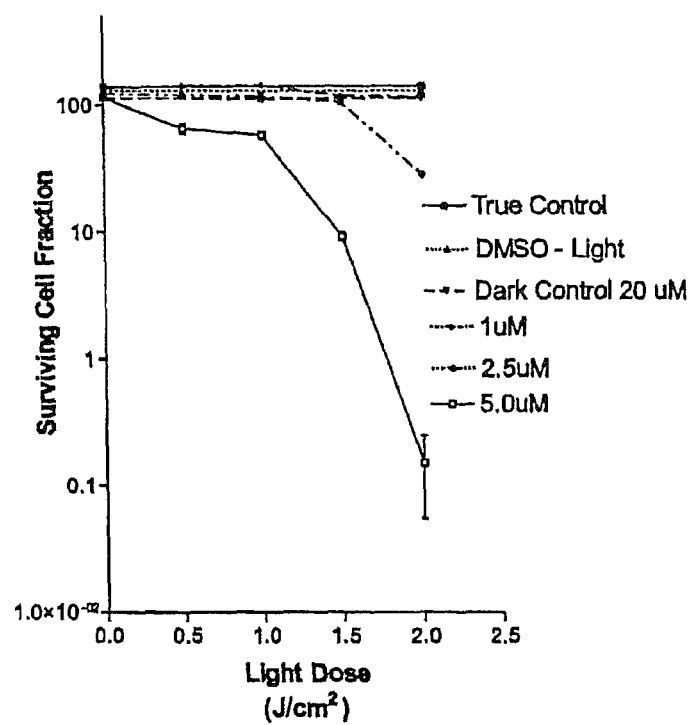
FIG. 9 is a graph showing the influence of a compound according to a preferred embodiment of the invention on EMT-6 cells, when the compound is submitted to a light treatment.
Figure 10:
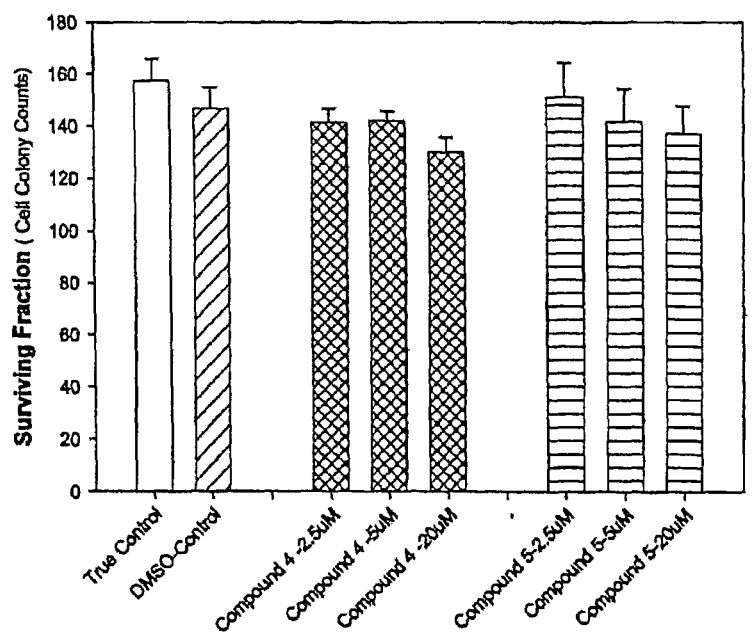
FIG. 10 is a graph comparing the results obtained concerning the toxicity on EMT-6 cells of the compounds analyzed in FIGS. 8 and 9.

As can be seen in FIGS. 8 and 9, both compounds (4) (FIG. 8) and (5) (FIG. 9) showed a dose dependent cell killing ability with increasing light and drug dose. Five μM drug concentration with 2 J/cm$^2$ light treatment has the most toxic effect giving cell survival of 1 cell per 1000 plated. The upper portion of the graph shows the drug effect without light delivery (dark toxicity). This shows that at even at the highest dose of 20 μM concentrations they have about 5 to 10% toxicity allowing an acceptable safety margin from non-treated to light treated samples.

Example 6

This example relates to the synthesis of 2-(N,N-dimethyl amino propyl)-amino-15-acetyl-3,10-dihydroxy-6,7,11-trimethoxy-14-methyl-15-H-cyclohepta(ghi)perylene-4,9-dione (4) and a 11,17 cyclized product (3) (Xu et al. *Bioorganic and Medicinal Chemistry Letters* 11, 2001, 2045-2047: Xu et al. *J of Photochemistry and Photobiology B: Biology*. 2003, 72, 61-67: Li et al *Biochimica et Biophysica Acta*. 2000, 1523, 6-12) by the mild reaction of hypocrellin B (2) and the 3-dimethylaminopropylamine (Scheme 1). Hypocrellin B (2) 2.5 gram was dissolved in 1.0 liter of dry tetrahydrofuran and to this mixture, 3-N,N-dimethylamino-propylamine (135 mL) was added by a dropping funnel over a period of 30 minutes at room temperature. The reaction mixture was stirred for 18 h at about 55 to 59° C. in the dark. After 18 h of stirring, the TLC and the mass spectrum of a sample of reaction mixture, showed the formation of the animated product, the solvent was removed by rotary evaporator under reduced pressure. The residue was subjected to high vacuum in order to remove the unreacted excess of the 3-dimethylamino-propylamine. Once the amine is removed, the dark colored residue was dissolved in minimum amount of the acetone and kept in the refrigerator. The crystals obtained after 24 h of cooling, are filtered and subjected to characterization. Mass and $^1$H NMR data showed it to be the cyclized product (3). The filtrate was concentrated and subjected to silica-gel column chromatography. The column was run in the gradient initially with CH$_2$Cl$_2$, then with 5% MeOH: CH$_2$Cl$_2$ and then 10% MeOH: CH$_2$Cl$_2$. All the fractions which were similar on the TLC and blue colored were pooled and concentrated on rotary evaporator and dried to give a dark colored solid 425 mg, which was recrystallized by acetone at 4-6° C. temperature, (93% purity on HPLC, Waters Symmetry C18 3.5 um, Mobile phase: 40% Phosphate buffer 20 mM/59.9 Acetonitrile/0.1% Triethylamine, final pH 7.2, Flow rate 1 mL/min, detection 465 nm, run: 10 min), with the retention time 1.39 min.

Characterization of Compound (3)

UV-VIS spectra (DMSO, conc. 50 μM, $\lambda_{max}$): 400, 500, 600 nm $^1$H NMR (CDCl$_3$, δ): 17.15 (s, 1H, OH), 17.85 (s, 1H, OH), 7.20 (s, 1H, 13-H), 6.75 (s, 1H, Ar—H), 6.60 (s, 1H, Ar—H), 4.62 (t, 2H, NCH$_2$CH$_2$CH$_2$N(CH$_3$)$_2$), 4.01, 4.10 (2s, 6H, OCH$_3$), 4.11 (s, 3H, OCH$_3$), 2.71 (s, 3H, 17-CH$_3$), 2.60 (s, 3H, 14-CH$_3$), 2.45 (t, 2H, NCH$_2$CH$_2$CH$_2$N(CH$_3$)$_2$), 2.30 (s, 6H, NCH$_2$CH$_2$CH$_2$ N(CH$_3$)$_2$), 2.15 (m, 2H, NCH$_2$CH$_2$CH$_2$N(CH$_3$)$_2$).

Mass spectra (m/z): 581.3 (M+1)

Characterization of Compound (4)

UV-VIS spectra (DMSO, conc. 50 μM, $\lambda_{max}$): 470, 580, 650 nm $^1$H NMR (CDCl$_3$, δ): 17.00 (s, 1H, OH), 16.45 (s, 1H, OH), 6.50 (s, 1H, Ar—H), 6.45 (s, 1H, Ar—H), 6.40 (s, 1H, 15-H), 6.20 (s, 1H, NHCH$_2$CH$_2$CH$_2$ N(CH$_3$)$_2$), 5.20 (s, 1H, 13-H), 4.20 (2s, 3H, OCH$_3$), 4.05 (s, 6H, OCH$_3$), 3.95 (m, 2H, NHCH$_2$CH$_2$CH$_2$N(CH$_3$)$_2$). 2.60 (t, 2H, NHCH$_2$CH$_2$CH$_2$N (CH$_3$)$_2$), 2.20 (s, 3H, 14-CH$_3$), 2.15 (s, 3H, 17-CH$_3$), 1.95 (t, 2H, NHCH$_2$CH$_2$CH$_2$N(CH$_3$)$_2$), 1.85 (s, 6H, NCH$_2$CH$_2$CH$_2$N(CH$_3$)$_2$).

Mass spectra (m/z): 599.3 (M+1).

Example 7

The second example relates to the synthesis of the (2,3b)-Octahydroquinoxalin-yl-hypocrellin B derivative with the migration of olefinic bond towards the cyclisation system from hypocrellin B (2) as shown in the scheme 2. Hypocrellin B (200 mg) was dissolved in 100 mL of freshly distilled tetrahydrofuran and to it 10 mL of 1,2-trans diaminocyclohexylamine was added drop wise over a period of ten minutes at room temperature. The resulting solution was stirred at 55-59° C. for 18 h in the dark. After 18 h of stirring the TLC and mass spectra was checked which showed the formation of the compound (Rf in EtOAC 0.45, and the mass corresponding to the mol. Wt of the cyclized product, 592). The reaction mixture was concentrated in vacuo under reduced pressure in the dark. The resulting dark colored reaction mixture was dissolved in CH$_2$Cl$_2$ (200 mL) and then washed with 0.1 N HCl three times (100 mL each) till the pH of the water layer is neutral. The organic layer was collected dried over sodium sulfate and filtered and concentrated to give a dark black colored residue which was subjected to silica gel column packed and eluted in Hexane, to remove the unreacted hypocrellin B. Then the column is eluted with acetone to elute the mixture of compound 5 and 6. The fractions were collected and concentrated to give a dark black residue which was subjected to preparative HPLC using C-18 reversed phase column to obtain compound 5 and 6. Compound 5 was obtained in two atropic isomers.

Characterization of Compound (5)

UV-VIS spectra (DMSO, conc. 50 μM, $\lambda_{max}$): 480, 585, 645 nm $^1$H NMR (CDCl$_3$, δ): 16.85 (brs, 2H, OH), 11.67 (s, 1H, NH), 11.62 (s, 1H, NH), 6.47 (s, 1H, 17-OH), 6.43 (s, 2H, Ar—H), 6.18 (t, 1H, 1'-H), 6.16 (t, 1H, 2'-H), 5.16 (s, 1H, 13-H), 4.01 (s, 3H, OCH$_3$), 4.00 (s, 3H, OCH$_3$), 3.96 (s, 3H, OCH$_3$), 2.30 (dd, 4H, 4' and 5'-H), 1.92 (brs, 4H, 3' and 6'-H), 1.66 (s, 3H, 17-CH$_3$), 1.49 (s, 3H, 14-CH$_3$).

Mass spectra (m/z): 591.1 (M−1).

Characterisation of Compound 6

$^1$H NMR (CDCl$_3$, δ): 16.85 (br s, 1H, OH), 11.91 (br s, 1H, NH), 6.39 (s, 1H, 5-H), 6.30 (s, 1H, 8-H), 5.97 (d, 1H, J=20 Hz, 15-H), 4.07 (s, 3H, OMe), 4.00 (s, 3H, OMe), 3.99 (d, 1H, J=14 Hz, 13-H), 3.95 (s, 3H, OMe), 3.38-3.00 (m, 3H), 2.23 (s, 4H), 2.10 (br s, 1H), 1.91 (br s, 2H), 1.50 (br s, 4H), 1.25 (s, 1H).

MS (m/z): 549.2 (M−1)

Example 8

(A) Pre-Clinical Characterization of Compound 4

(1) Photodynamic Activity of Compound 4

Figure 13:
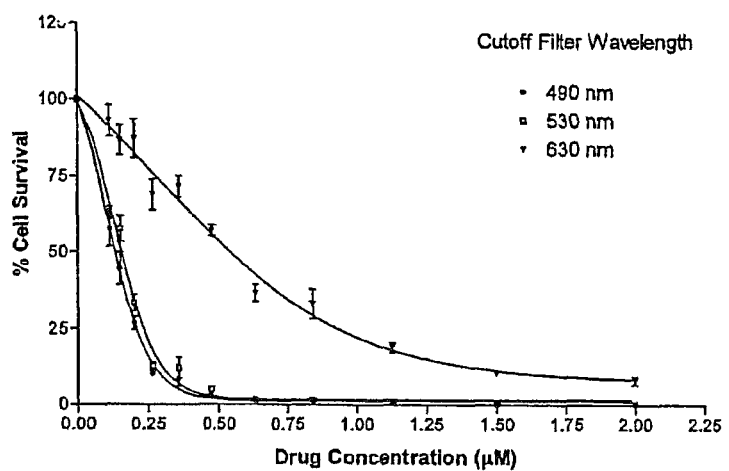
FIG. 13 is a graph of cell survival as measured by thymidine uptake of BT549 cells treated with a compound according to a preferred embodiment of the invention and radiation at the indicated wavelength.

The photodynamic activity of compound 4 has been studied in two cell lines cells by measuring cell death post treatment by tritiated thymidine uptake (in 81549 cells) and clonogenic assays (in EMT-6 cells). The results are shown in FIG. 13 and FIG. 8. These tests indicate compound 4 cause significant cell death after light treatment. No significant activity is seen in the absence of light treatment confirming the selectively of the PDT effect.

(2) Uptake of Topically Applied Gel of Compound 4

Figure 14:
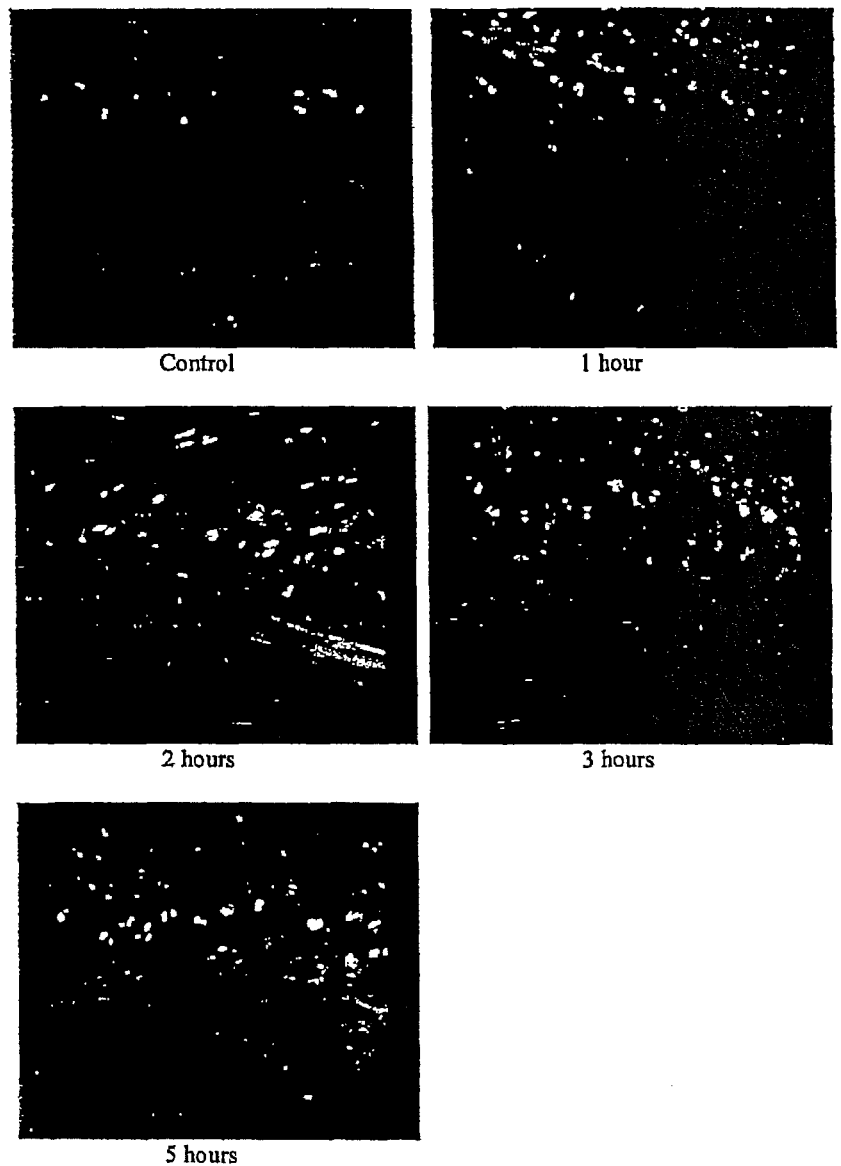
FIG. 14 shows histological slides of a skin sample showing the penetration of a compound according to a preferred embodiment of the invention.

The uptake of topically applied compound 4 Gel was studied using normal mouse skin as a model. The penetration of compound 4 into the epidermal layer of the murine skin was demonstrated by the presence of fluorescence in the treated samples. The results are shown in FIG. 14. The drug penetrated the epidermis after one hour and remained localized in the area up to 5 hours, a slight increase in the muscle layer was seen at the end of 5 hours. The results suggested that uptake of the photosensitizer in the epidermal layer appeared optimal at 2 to 3 hours post application.

(3) Effect of Compound 4 on Normal Mouse Skin

Light treatment alone without the photosensitizer did not cause any tissue damage up to the 100 $J/cm^2$ light dose used. Likewise, the photosensitizer alone without light treatment was also ineffective. At the lower light dose (70 $J/cm^2$), mild injury to the epidermal cells was observed 7 days post treatment with a penetration time of 1 or 2 hours. When the photosensitizer was allowed to penetrate for 3 to 5 hours, significant epidermal apoptosis was observed. When the light dose was increased to 100 $J/cm^2$, the PDT treatment caused tissue damage in a manner escalating with longer incubation times. After 1 hour of penetration, only the epithelium and part of the fatty layer showed damage. Apoptosis of epidermal cells, basal layer and hair follicle was seen after 2 hours of penetration. After 3 hours of penetration, the whole tissue layer, including muscle layer showed significant damage.

(4) Effects of Compound 4 on Animals with Pre-Cancerous Skin Lesions or Small Tumors An experiment targeted animals with pre-cancerous skin lesions or small tumors using ACP-compound 4 Topical Gel (3 hour penetration) at a light dose of 100 $J/cm^2$ was performed. Two animals were sacrificed two weeks after one light treatment; two animals received a second light treatment at week 2 and were sacrificed 14 days later at week 4. The combination of Topical gel of compound 4 with 100 $J/cm^2$ light treatment caused apoptosis of the in situ portion of the epidermal malignancy. More intense apoptotic changes were observed with the animals which received 2 light treatments.

TABLE 1

Summary of PDT Treatment Results

| Treatment | Response Rate |
|---|---|
| 0.5% ACP-compound 4 One Light Treatment | 1/3 (33%) |
| 0.5% ACP-compound 4 Two Light Treatments | 6/6 (100%) |
| 1% ACP-compound 4 One Light Treatment | 9/12 (75%) |
| 1% ACP-compound 4 Two Light Treatments | 8/10 (80%) |

Figure 15:
FIG. 15 shows histological slides of a skin sample showing the penetration of a compound according to a preferred embodiment of the invention.
Figure 15:
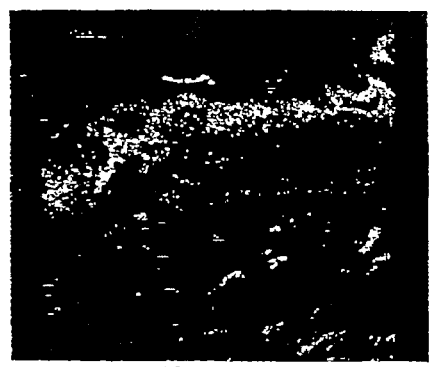

(5) Effects of Compound 4 on Human (Ex Vivo) Skin Samples from Patients Undergoing Breast or Abdominal Reduction Surgery Human (ex vivo) skin samples were obtained from patients undergoing breast or abdominal reduction surgery and were treated with compound 4 Topical Gel for 10 minutes, 1, 3, 5 or 24 hours. Fluorescence analysis demonstrated complete dermal penetration by 3-5 hours (FIG. 15).

(6) Effects of Compound 4 on PDT Treated Human (Ex Vivo) Skin Sample.

An analysis of PDT treated human (ex vivo) skin samples showed no histological changes up to two days post treatment but progressive necrotic/apoptotic changes thereafter.

(7) Toxicological Study on Compound 4

A toxicological study was performed under GLP in male and female rats using up to 12.5 mg/kg of ACP-compound 4 administered intravenously. No toxicologically significant treatment related clinical observations, hematology, coagulation, clinical biochemistry, urinalysis, necropsy and tissue histopathology effects were observed at any point up to the 14 day termination period. A dermatological toxicology study was performed under GLP in male and female rabbits using approximately 0.36 $mg/cm^2$ (total exposed dose of 92 mg) of ACP-compound 4 administered to the skin as a topical gel formulation (4%) with 3 doses repeated every week for three weeks. No toxicologically significant treatment related clinical observations, hematology, clinical biochemistry, necropsy and tissue histopathology effects were observed at any point up to the 22 day termination period.

Example 9

Phase 1 Clinical Study with ACP-Compound 4 Topical Gel For Photodynamic Therapy of Actinic Keratosis The study consists of 4 groups of 3 patients in a controlled, randomized, open label, dose escalation study. The primary objective of the study was to determine the cutaneous and systemic toxicity of compound 4 with and without photoactivation. The study also explores clinically and pathologically the therapeutic effect of PDT with compound 4 on actinic keratosis.

With up to 8 out of the 12 required patients enrolled in the study, the drug and PDT treatment were well tolerated so far. No adverse events were observed to date.

Example 10

Phase 1 Clinical Study

Histological Localization of ACP-Compound 4 after Topical Application to the Back of Patients with Acne The primary objective of the study was to measure and quantify the fluorescence levels of ACP-compound 4 in sebaceous glands, epidermis and hair follicles at different time points after topical application. The study also monitored the safety of the drug product after topical administration. The study consisted of a group of 10 patients with acne on the back. No adverse events have been observed with the drug application.

Example 11

Pre-Clinical Characterization of ACP-Compound 5

(1) Photodynamic Activity of Compound 5

Figure 16:
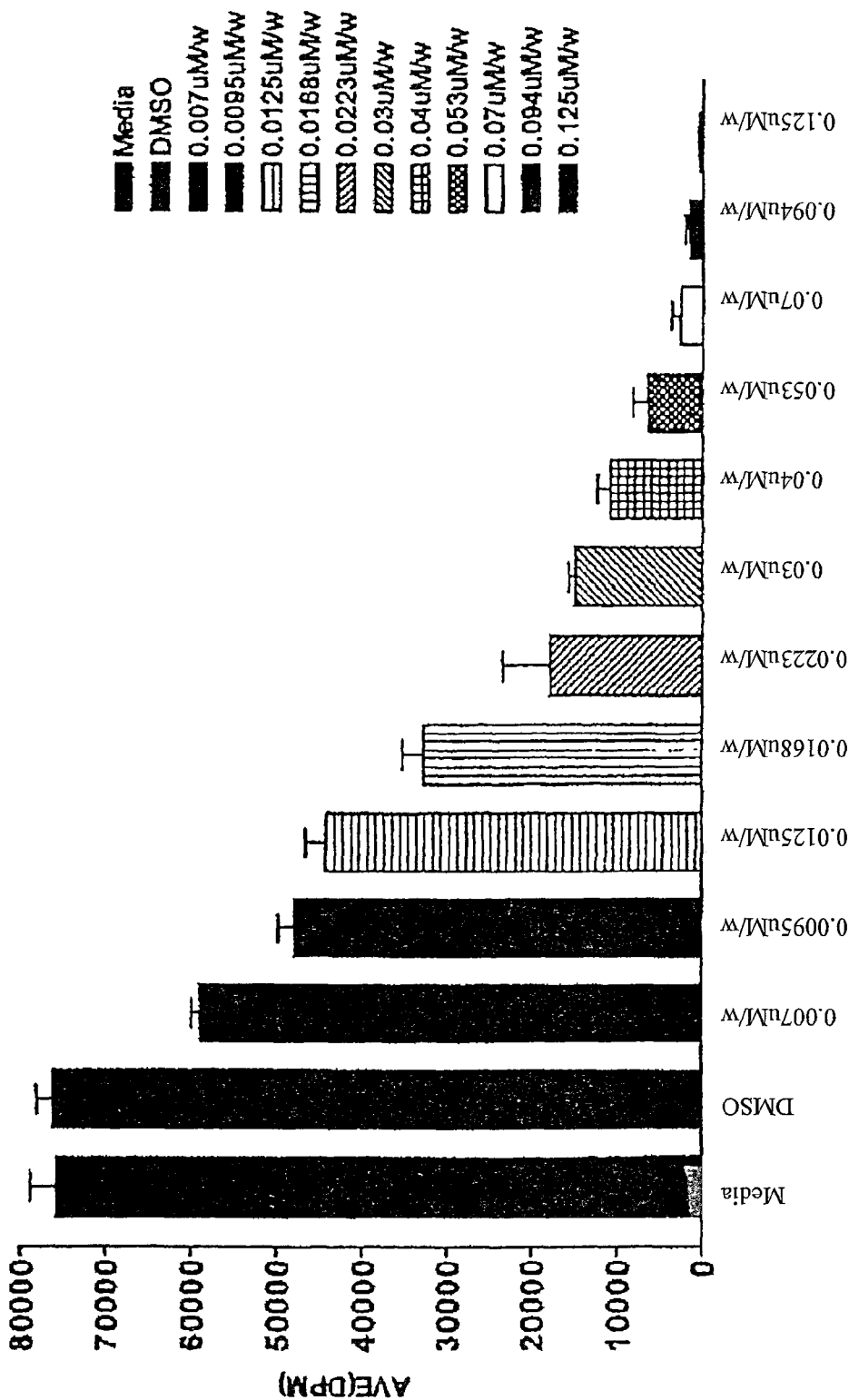
FIG. 16 is a graph of cell survival as measured by thymidine uptake of BT549 cells treated with a compound according to a preferred embodiment of the invention and radiation.
Figure 17:
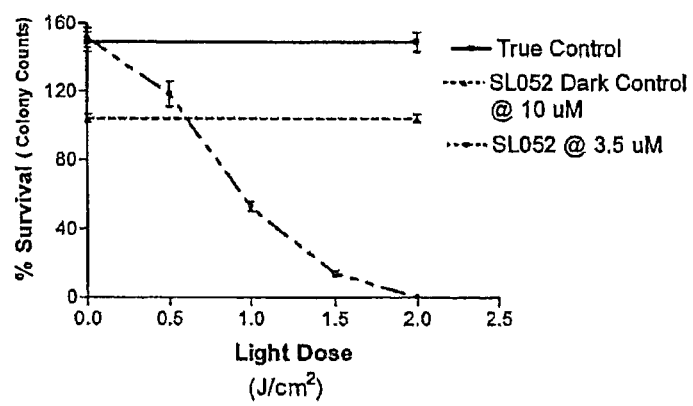
FIG. 17 is a graph of EMT6 cell survival upon photodynamic treatment with a compound according to a preferred embodiment of the invention as measured by a clonogenic assay.

The photodynamic activity of ACP-compound 5 was studied in two cell lines cells by measuring cell death post treatment by tritiated thymidine uptake (in BT549 cells) and clonogenic assays (in EMT-6 cells). The results are shown in FIGS. 16 and 17. These tests indicate ACP-compound 5 caused significant cell death after light treatment. No significant activity is seen in the absence of light treatment confirming the selectively of the PDT effect.

(2) Effect of Compound 5 on PDT Treated EMT-6 Mouse Tumor Model

Figure 18:
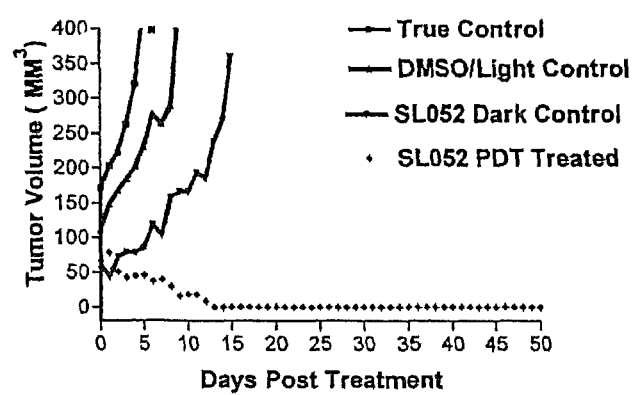
FIG. 18 is a graph of the volume of an EMT6 tumor model as a function of time after photodynamic treatment with a compound according to a preferred embodiment of the invention administered as a liposomal composition.
Figure 19:
FIG. 19 shows photographs of a mouse skin tumor before and after photodynamic therapy with a compound according to a preferred embodiment of the invention.
Figure 19:
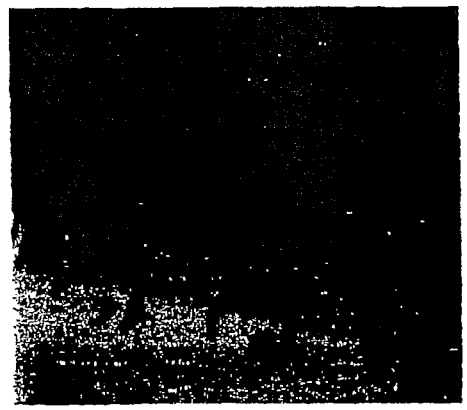
Figure 19:
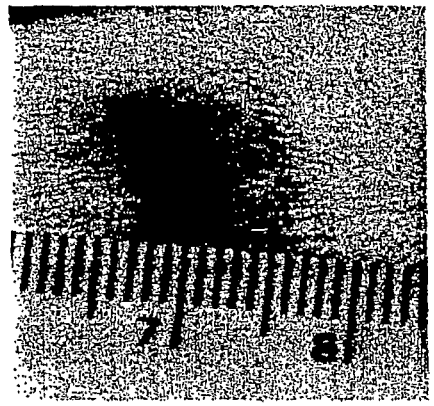

Liposomal formulations of compound 5 for systemic delivery of the photosensitizer. The photosensitizer is formulated with a mixture of dipalmitoyl phosphatidylcholine (DPPC) and cholesterol and extruded through membrane of different pore size until the required size of liposomes was achieved. The uptake and efficacy of the PDT treatment was demonstrated in-vivo using an EMT-6 mouse tumor model. Complete cure of the implanted tumor is achieved only by combining compound 5 with light treatment confirming the specificity of the treatment modality. The study results are shown in FIGS. 18 and 19.

(3) Effects of Compound 5 on PDT Treated R3327-AT Left Flank Tumor in Rat.

Male Fisher-Copenhagen rats were given a sub-cutaneous R3327AT left flank tumor implant under anesthesia. The animals were allowed to recover and the tumor to develop to an approximate volume of 1500 to 2500 mm$^3$.

The rats were given an I.V. injection of compound 5 liposomal formulation and allowed to recover for a 2.5 to 3 hour prior to light treatment. The total light dose delivered was in the range of 0.5 to 1.0 Joules/mm$^3$ of tumor volume.

Figure 20:
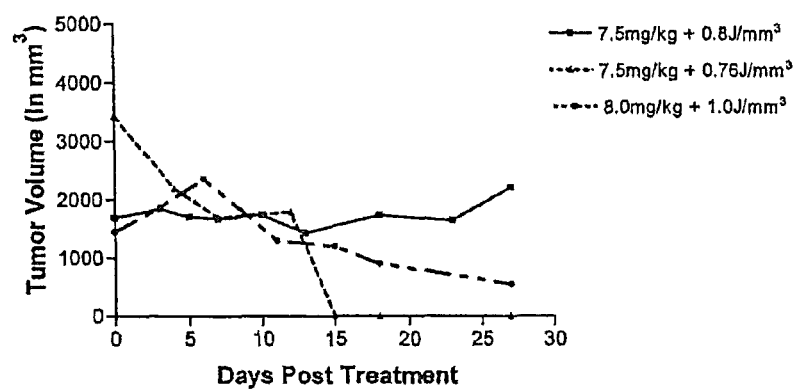
FIG. 20 is a graph of the volume of R3327-A AT flank tumor in a rat as a function of time after photodynamic treatment with a compound according to a preferred embodiment of the invention administered as a liposomal composition.
Figure 21:
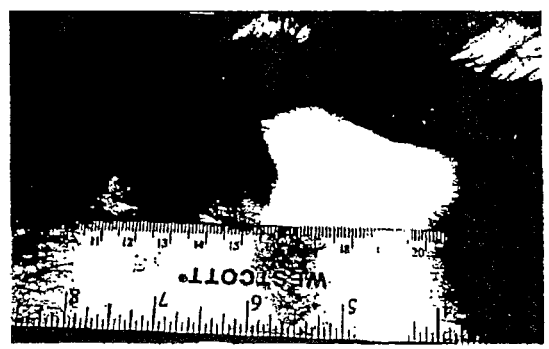
FIG. 21 is a photograph showing post photodynamic therapy tumor necrosis.

The tumor size was monitored by caliper measurements which allowed total tumor volume calculation. The endpoints were either tumor "cure" or when the tumor mass had reached 4 times the initial treatment volume. The results are shown in FIGS. 20 and 21.

Example 12

Sonodymanic Therapy with Compound 5

Sonodynamic Activity on HL-60 Cells.

Figure 22:
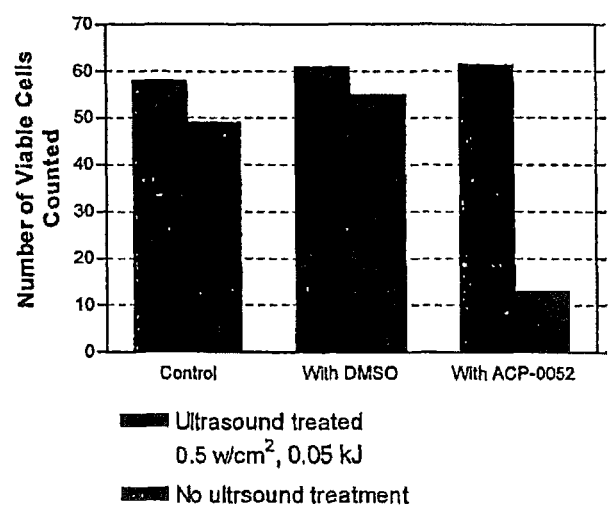
FIG. 22 is a bar graph showing the effect of sonodynamic therapy of HL-60 cells with a compound according to a preferred embodiment of the invention.

The effect of SDT treatment with compound 5 on HL-60 cell suspension was monitored by cell counting with trypan blue exclusion to monitor viable cell count pre and post ultrasound treatment (FIG. 22).

Clonogenic Assay with EMT-6 cells for detection of sonodynamic activity of compound 5

Figure 23:
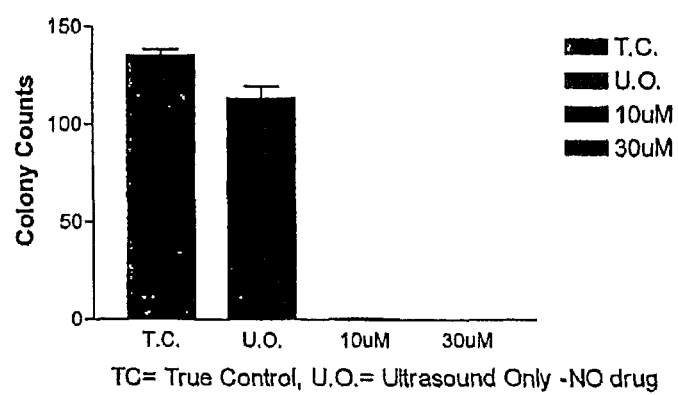
FIG. 23 is a graph of EMT6 cell survival after sonodynamic treatment with a compound according to a preferred embodiment of the invention as measured by a clonogenic assay.

Clonogenic assay with EMT-6 cells was used to study the effect of ultrasound treatment with compound 5. The EMT-6 cells are incubated with compound 5 at different concentrations for 4 hours followed by 30 seconds of ultrasound treatment at 0.5 W/cm2 (1 MHz). The treated cells and the untreated controls were trypsinized and replated in normal growth media at known quantities and allowed to grow for 7 days. The number of colonies formed was then counted and the results are shown in FIG. 23.

In-Vivo SDT in Murine Peritoneal Carcinotamosis Model

Male Balb-c mice were given a priming dose of 400 micro liters of Pristane. Thirteen days later, they were given an intra-peritoneal injection of 5×10$^6$ SP/2 cells. drug/ultrasound Five control mice were left untreated after tumor implant. Five days post tumor implant, the SDT treatment group were given an intra-peritoneal injection of 50 mg/kg compound 5 in liposomal formulation in Hank's balanced salt solution (total volume=0.75 ml). The mice were allowed a 4 hour drug uptake time in subdued lighting. They were then anaesthetized with sodium pentobarbital and subjected to an ultrasound treatment at 1 mega-hertz using a 50 milli-watt power level for 5 cycles of 2 minutes duration on then a 1 minute off period to give a total delivered dose of 1.5 Kilo-Joules. The animals were allowed to recover and kept in subdued lighting for a further 24 hours to allow for drug metabolism/excretion.

Figure 24:
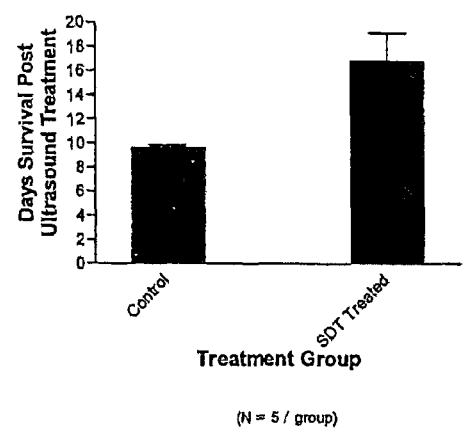
FIG. 24 is a bar graph showing the increase survival of mice with abdominal ascities producing tumors after sonodynamic therapy with a compound according to a preferred embodiment of the invention.

The mice were monitored daily for general health and body weights. When the abdomen was noticeably swollen an abdominal "tap" was performed to drain off excess fluid. The experimental end point was when the animals became visibly distressed or death resulted through the over-night period. The results are shown in the FIG. 24.

Figure 25:
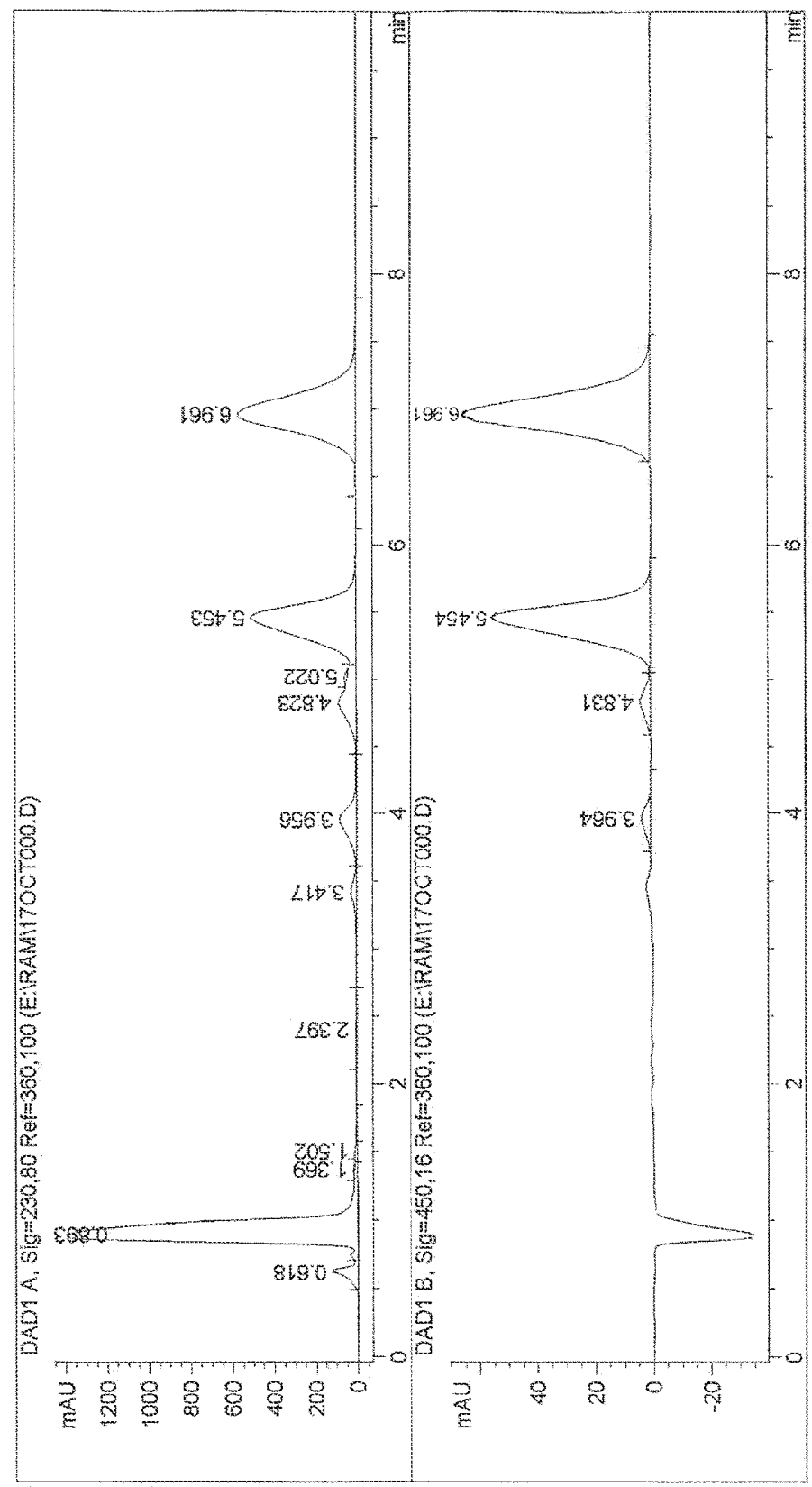
FIG. 25 is an HPLC chromatogram showing the separation of atropisomers of a compound according to a preferred embodiment of the invention.

(4) Separation of Atropisomers of Compound 5 by High Pressure Liquid Chromatography The atropisomers of compound 5 was separated and isolated by High Pressure Liquid Chromatography (HPLC). The following condition were applied and a sample HPLC trace is shown in FIG. 25.

HPLC Analysis Conditions:

$C_{18}$ 3.5 μm; 4.6×75 mm column

Mobile phase: 20 mM phosphate-acetonitrile-triethylamine

Flow Rate: 1 mL/min

Detection: 230 nm and 465 nm

Retention Time of atropisomers: 5.46 and 6.96 min

The references cited in this application are hereby incorporated by references. The person skilled in the art would recognize that various modifications, adaptations, and variations may be brought to the previously presented preferred embodiments without departing from the scope of the following claims.

The invention claimed is:

1. A method for carrying out a therapy on a subject in need thereof comprising:
   a) administering to the subject a compound of formula (Ia) or (Ib) or stereoisomer or atropisomer thereof:

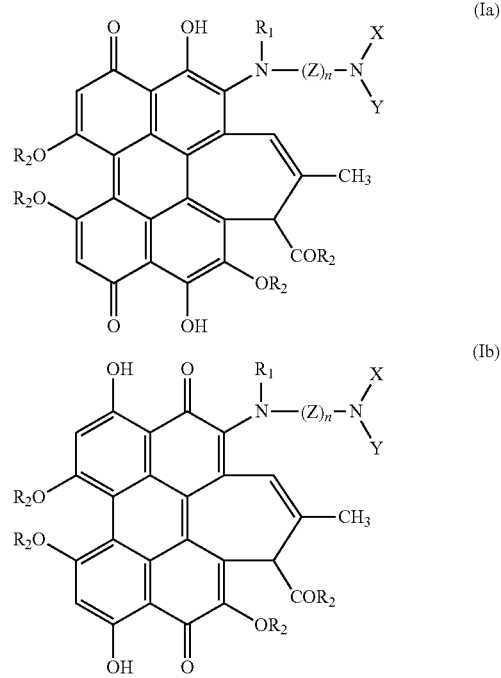

wherein:

X and Y are independently hydrogen, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, $C_1$-$C_{12}$ heteroaryl, —$COR_1$, —$(CH_2)_mOR_1$, —$CO_2H$, —$CO_2R_1$, —$C(O)N(R_1)_2$, —$C(O)NH(R_1)$, or —$C(O)NH_2$, said $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl being unsubstituted or substituted with at least one substituent selected from the group consisting of a halogen atom, hydroxy, carboxy, thiol, azide, nitro, $C_1$-$C_8$ deuterated alkyl group comprising at least one deuterated atom, —COH, —$COR_1$, —$(CH_2)_mOR_1$, —$CO_2H$, —$CO_2R_1$, —$C(O)N(R_1)_2$—$C(O)NH(R_1)$, —$C(O)NH_2$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl;

Z is —$CH_2$—, —$CHR_3$—, —$CH_2$—CH═CH—, —$CHR_3$—CH═CH—, or —$CH_2$—CH═$CR_3$—;

$R_1$ is a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

each $R_2$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

$R_3$ is halogen atom, hydroxy, sulphydral(—SH), an amino acid residue, carboxy, thiol, azide, nitro, $SO_3H$, —COH, —$COR_1$, —$(CH_2)_mOR_1$, —$CO_2H$, —$CO_2R_1$, —$C(O)N(R_1)_2$—$C(O)NH(R_1)$, —$C(O)NH_2$, —$HNC(O)R_1$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, or $C_1$-$C_{12}$ heteroaryl;

n is an integer having a value of 1 to 13; and
m is an integer having a value of 1 to 13,
or a pharmaceutically acceptable salt thereof; and,
b) activating a target area in the subject with a light having a wavelength suitable for activating said compound or an ultrasound suitable to activate said compound.

2. The method of claim 1, wherein said target is selected from the group consisting of a tissue, diseased tissue and microorganism.

3. The method of claim 2, wherein said tissue is selected from the group consisting of epithelium, connective tissue, muscle tissue and nervous tissue.

4. The method of claim 2, wherein said diseased tissue is a hyperproliferative tissue.

5. The method of claim 4, wherein said hyperproliferative tissue is selected from the group consisting of, an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumors of a lung, a skin tumor, a nonsolid tumor and malignant cells of one of a hematopoietic tissue and a lymphoid tissue.

6. The method of claim 2, wherein said diseased tissue is selected from the group consisting of lesions in a vascular system, a diseased bone marrow, a pre-cancerous lesion, a skin disease, diseased cells in which the disease is one of an autoimmune and an inflammatory disease.

7. The method of claim 6, wherein said skin disease is selected from the group consisting of actinic keratosis, acne, psoriasis and eczema.

8. The method of claim 2, wherein said microorganism target is selected from the group consisting of bacteria, viruses, fungi and protozoa.

9. The method of claim 1, further comprising the step of allowing sufficient time for said compounds that are not associated to the target tissue to clear from non-target tissue of the subject prior to the step of irradiating.

10. The method of claim 1, wherein the compound is conjugated to a targeting agent.

11. The method of claim 10, wherein the targeting agent is an antibody or an antibody fragment that is specific in binding with the target.

12. The method of claim 10, wherein the targeting agent is a peptide that is specific in binding with the target.

13. The method of claim 10, wherein the targeting agent is a liposomal preparation.

14. The method of claim 1, wherein said administration is selected from the group consisting of intravenous, subcutaneous, intraperitoneal, intrathecal, intravesical, intradermal, intramuscular, intraarterial, intralymphatic routes, rectal, topical, mucosal and transmucosal.

15. The method of claim 14, wherein said subject is a human.

16. A method for detecting the presence of a target in a subject comprising:
a) administering to the subject a compound of formula (Ia) or (Ib) or stereoisomer or atropisomer thereof:

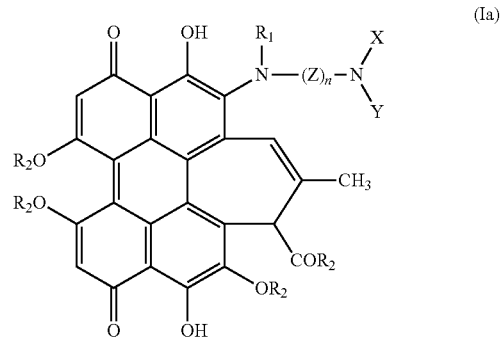

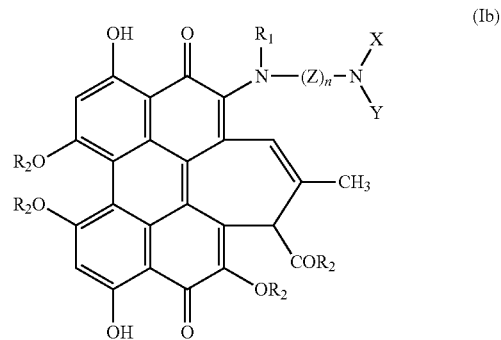

wherein:
X and Y are independently hydrogen, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, $C_1$-$C_{12}$ heteroaryl, —$COR_1$, —$(CH_2)_mOR_1$, —$CO_2H$, —$CO_2R_1$, —$C(O)N(R_1)_2$, —$C(O)NH(R_1)$, or —$C(O)NH_2$, said $C_1$-$C_8$ alkyl, $C_2$-$C_8$ alkenyl, $C_2$-$C_8$ alkynyl $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl being unsubstituted or substituted with at least one substituent selected from the group consisting of a halogen atom, hydroxy, carboxy, thiol, azide, nitro, $C_1$-$C_8$ deuterated alkyl group comprising at least one deuterated atom, —COH, —$COR_1$, —$(CH_2)_mOR_1$, —$CO_2H$, —$CO_2R_1$, —$C(O)N(R_1)_2$—$C(O)NH(R_1)$, —$C(O)NH_2$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, and $C_1$-$C_{12}$ heteroaryl;

Z is —$CH_2$—, —$CHR_3$—, —$CH_2$—CH=CH—, —$CHR_3$—CH=CH—, or —$CH_2$—CH=$CR_3$—;

$R_1$ is a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

each $R_2$ is independently a hydrogen atom, $C_1$-$C_8$ alkyl, $C_3$-$C_8$ cycloalkyl, $C_4$-$C_{10}$ cycloalkenyl, $C_6$-$C_{12}$ aralkyl, or $C_1$-$C_{12}$ heterocyclyl;

$R_3$ is halogen atom, hydroxy, sulphydral(—SH), an amino acid residue, carboxy, thiol, azide, nitro, $SO_3H$, —COH, —$COR_1$, —$(CH_2)_m OR_1$, —$CO_2H$, —$CO_2R_1$, —C(O)N$(R_1)_2$—C(O)NH$(R_1)$, —C(O)$NH_2$, —HNC(O)$R_1$, $C_1$-$C_8$ alkyl, $C_2$-$C_8$ alkenyl, $C_2$-$C_8$ alkynyl, $C_3$-$C_8$ cycloalkyl, $C_4$-$C_{10}$ cycloalkenyl, $C_6$-$C_{12}$ aryl, $C_6$-$C_{12}$ aralkyl, $C_1$-$C_{12}$ heterocyclyl, or $C_1$-$C_{12}$ heteroaryl;

n is an integer having a value of 1 to 13; and m is an integer having a value of 1 to 13, or a pharmaceutically acceptable salt thereof; and, b) visualizing the compound within the subject.

17. The method of claim 16, wherein in step (a), said compound associates with said target.

18. The method of claim 16, wherein said target is selected from the group consisting of a tissue, diseased tissue and microorganism.

19. The method of claim 18, wherein said tissue is selected from the group consisting of epithelium, connective tissue, muscle tissue and nervous tissue.

20. The method of claim 18, wherein said diseased tissue is a hyperproliferative tissue.

21. The method of claim 20, wherein said hyperproliferative tissue is selected from the group consisting of, an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumors of a lung, a skin tumor, a nonsolid tumor and malignant cells of one of a hematopoietic tissue and a lymphoid tissue.

22. The method of claim 18, wherein said diseased tissue is selected from the group consisting of lesions in a vascular system, a diseased bone marrow, a pre-cancerous lesion, a skin disease, diseased cells in which the disease is one of an autoimmune and an inflammatory disease.

23. The method of claim 18, wherein said microorganism target is selected from the group consisting of bacteria, viruses, fungi and protozoa.

24. The method of claim 16, wherein said step (b) is carried out by a method selected from MRI imaging of at least a part of the subject's body, nuclear imaging and fluorescence detection of the compound.

25. The method of claim 16, wherein said target is in a biological sample.

26. The method of claim 25, wherein the biological sample is selected from the group consisting of blood, urine, saliva, tears, synovial fluid, sweat, interstitial fluid, sperm, cerebrospinal fluid, ascites fluid, tumor tissue, biopsy and circulating tumor cells.

27. The method of claim 16, wherein said compound is conjugated to a target agent specific for said target.

28. The method of claim 16, wherein sufficient time is allowed for molecules that are not associated to the target to clear from non-target tissue of the subject.

29. The method of claim 16, wherein said administration is selected from the group consisting of intravenous, subcutaneous, intraperitoneal, intrathecal, intravesical, intradermal, intramuscular, intraarterial, intralymphatic routes, rectal, topical, mucosal and transmucosal.

30. The method of claim 29, wherein said subject is a human.

* * * * *

UNITED STATES PATENT AND TRADEMARK OFFICE
CERTIFICATE OF CORRECTION

| | | |
|---|---|---|
| PATENT NO. | : 8,747,811 B2 | Page 1 of 1 |
| APPLICATION NO. | : 14/012865 | |
| DATED | : June 10, 2014 | |
| INVENTOR(S) | : Sanjay K. Sharma | |

It is certified that error appears in the above-identified patent and that said Letters Patent is hereby corrected as shown below:

On the Title Page
Item (60)
The filing date of application No. 11/722,423 is missing. The filing date of June 21, 2007 should be added.

Signed and Sealed this
Seventh Day of October, 2014

Michelle K. Lee
*Deputy Director of the United States Patent and Trademark Office*